(12) United States Patent
Minamitani

(10) Patent No.: US 10,436,701 B2
(45) Date of Patent: Oct. 8, 2019

(54) CORROSION ENVIRONMENT DIAGNOSIS SYSTEM, CORROSION PREVENTION SYSTEM, CORROSION ENVIRONMENT DIAGNOSIS METHOD, AND CORROSION PREVENTION METHOD

(71) Applicant: Hitachi, Ltd., Chiyoda-ku, Tokyo (JP)

(72) Inventor: Rintarou Minamitani, Tokyo (JP)

(73) Assignee: HITACHI, LTD., Tokyo (JP)

( * ) Notice: Subject to any disclaimer, the term of this patent is extended or adjusted under 35 U.S.C. 154(b) by 202 days.

(21) Appl. No.: 15/539,361

(22) PCT Filed: Dec. 26, 2014

(86) PCT No.: PCT/JP2014/084504
§ 371 (c)(1),
(2) Date: Jun. 23, 2017

(87) PCT Pub. No.: WO2016/103445
PCT Pub. Date: Jun. 30, 2016

(65) Prior Publication Data
US 2017/0350807 A1    Dec. 7, 2017

(51) Int. Cl.
*G01N 17/00* (2006.01)
*G01B 7/06* (2006.01)
(Continued)

(52) U.S. Cl.
CPC .............. *G01N 17/00* (2013.01); *F24F 11/30* (2018.01); *G01B 7/06* (2013.01); *G01B 7/066* (2013.01);
(Continued)

(58) Field of Classification Search
CPC .... G01N 17/00; G01N 17/002; G01N 27/416; G01B 7/06; G01B 7/066; G01B 17/02;
(Continued)

(56) References Cited

U.S. PATENT DOCUMENTS 6,110,355 A * 8/2000 Hiramoto ............... G01N 17/02
205/763

FOREIGN PATENT DOCUMENTS

JP    2010-038838 A     2/2010
JP    2010038838 A *    2/2010
(Continued)

OTHER PUBLICATIONS

ANSI/ISA 71.04-2013, Environmental Conditions for Process Measurement and Control Systems: Airborne Contaminants Research Triangle Park: International Society for Automation.
(Continued)

*Primary Examiner* — Marc E Norman
(74) *Attorney, Agent, or Firm* — Foley & Lardner LLP

(57) ABSTRACT

The present invention is a corrosion environment diagnosis system including: an environment measuring device that includes a temperature sensor that measures temperature in an electronic part serving as a diagnosis target or an indoor space in which an electronic device including the electronic part is installed, a humidity sensor that measures relative humidity in the indoor space or the electronic device, a corrosion sensor that measures a corrosion thickness of the diagnosis target, and a database in which indoor environment data including the temperature and the relative humidity measured by the temperature sensor and the humidity sensor and corrosion thickness data including the corrosion thickness measured by the corrosion sensor are accumulated; an outside air environment database in which outside air environment data including previous temperature and humidity of outside air is recorded; and a diagnostic processing device capable of receiving data of the outside air environment database and the environment measuring device, wherein the diagnostic processing device decides a corrosion mechanism corresponding to a relation between
(Continued)

the corrosion thickness and the relative humidity on the basis of the indoor environment data, the corrosion thickness data, and the outside air environment data, and estimates a future corrosion thickness of the diagnosis target. Accordingly, it is possible to accurately estimate a future corrosion thickness on the basis of a mechanism of corrosion by atmospheric air including corrosive gas.

11 Claims, 16 Drawing Sheets

(51) Int. Cl.
    *G01B 17/02*     (2006.01)
    *G01K 1/14*     (2006.01)
    *G01N 27/416*     (2006.01)
    *H05K 7/20*     (2006.01)
    *F24F 11/30*     (2018.01)
    *F24F 110/10*     (2018.01)
    *F24F 110/12*     (2018.01)
    *F24F 110/20*     (2018.01)
    *F24F 110/22*     (2018.01)

(52) U.S. Cl.
    CPC ............... *G01B 17/02* (2013.01); *G01K 1/14* (2013.01); *G01N 17/002* (2013.01); *G01N 27/416* (2013.01); *H05K 7/20836* (2013.01); *F24F 2110/10* (2018.01); *F24F 2110/12* (2018.01); *F24F 2110/20* (2018.01); *F24F 2110/22* (2018.01); *H05K 7/20745* (2013.01)

(58) Field of Classification Search
    CPC ........ F24F 11/30; F24F 2110/10; F24F 11/12; F24F 11/20; F24F 11/22; G01K 1/14; H05K 7/20745; H05K 7/20836
    See application file for complete search history.

(56) References Cited

FOREIGN PATENT DOCUMENTS

| JP | 4599439 B2 | 12/2010 |
|---|---|---|
| JP | 2011-039011 A | 2/2011 |
| JP | 2011-058907 A | 3/2011 |
| JP | 2012-189356 A | 10/2012 |

OTHER PUBLICATIONS

ASHRAE TC9.9, "2011 Gaseous and Particulate Contamination Guidelines for Data Centers".
Craig Hillman: Silver and Sulfur: Case Studies, Physics, and Possible Solusions, SMTA International Conference 2007 Proceedings.
ISO 11844-1, 2006, Corrosion of Metals and Alloys-classification of Low Corrosivity Indoor Atmospheres—Part1: Determination and Estimation of Indoor Corrosivity. Geneve, Suisse: International Organization of Standardization.
Minamidani: Proposal of Interpretation of Atmospheric Air Corrosion Mechanism of Silver and Corrosion Prediction Method: Material and Environment 2014 Lecture Proceedings, pp. 345-348, Published on Apr. 30, 2014 (in Japanese).
International Search Report dated Mar. 24, 2015 as issued in International Application No. PCT/JP2014/084504.

\* cited by examiner

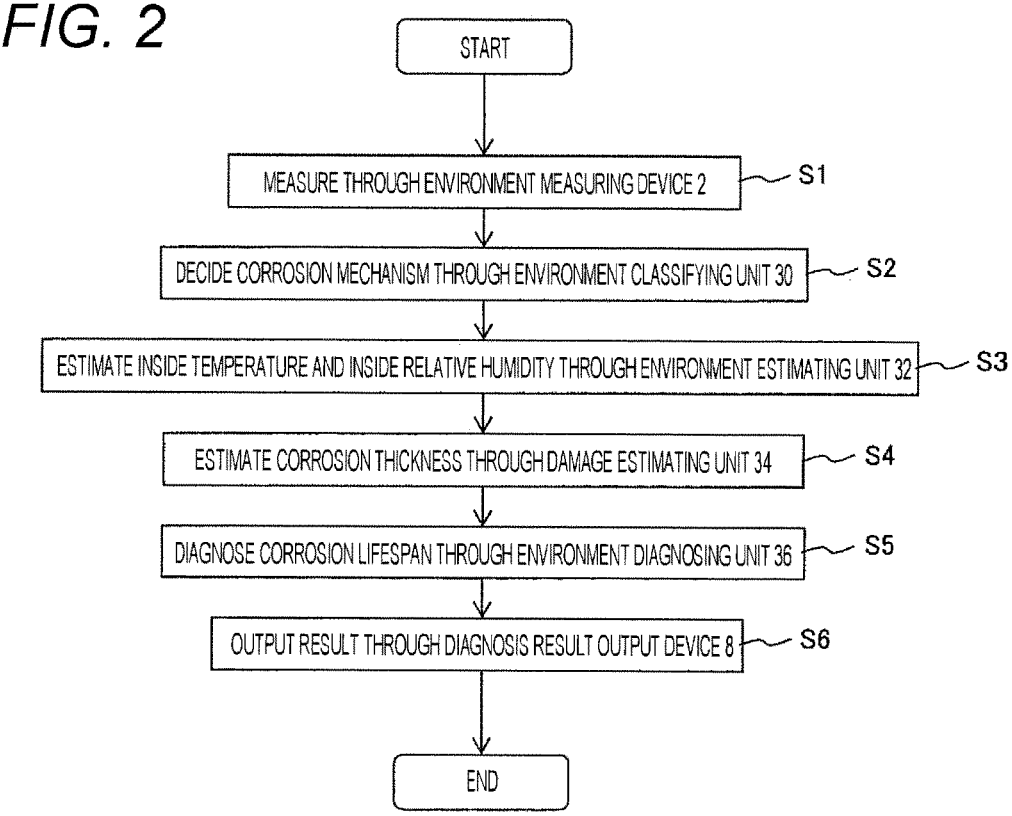
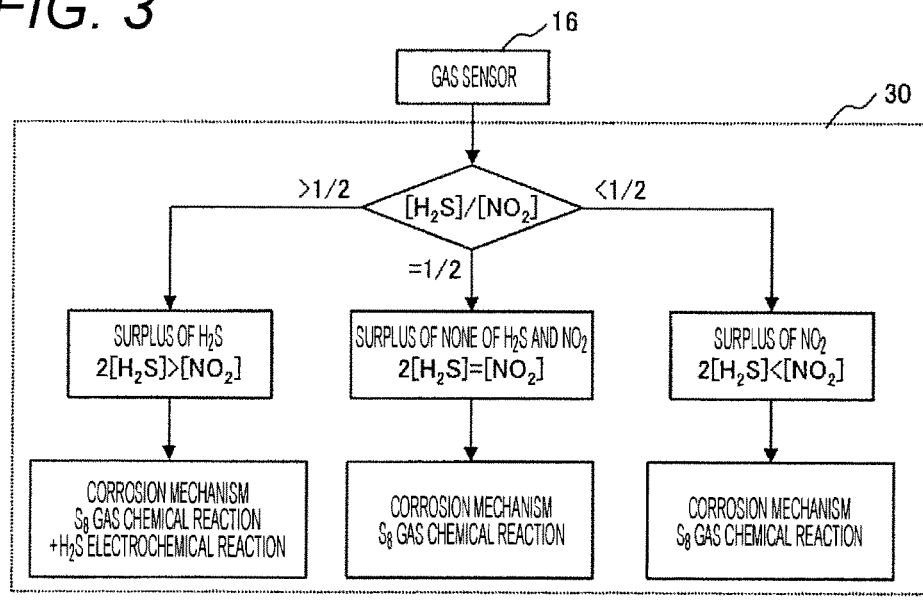

FIG. 12

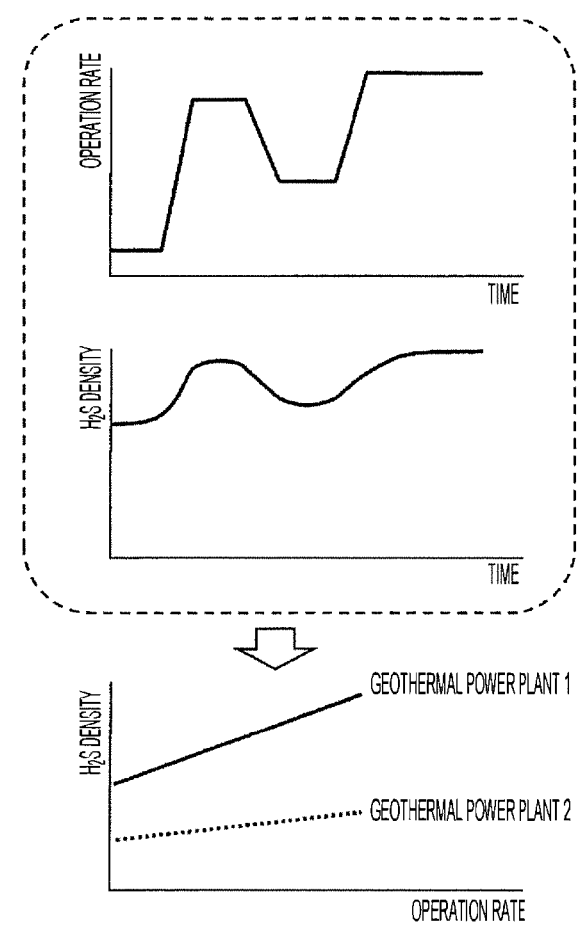

FIG. 13

| STEEL PLANT |
|---|
| STRUCTURE DATA · ROOM SIZE · POSITION OF AIR CONDITIONER · POSITION OF FILTER · INSTALLATION POSITION OF SENSOR · INSPECTION TARGET POSITION | ENVIRONMENT DATA · TEMPERATURE · RELATIVE HUMIDITY · OUTSIDE AIR TEMPERATURE AND HUMIDITY · CORROSIVE GAS DENSITY OR COEFFICIENT C · SETTING OF AIR CONDITIONER · CAPABILITY OF FILTER | OPERATION DATA · OPERATION RATE · PROCESSING CAPABILITY (UPPER LIMIT VALUE OF GAS OCCURRENCE) |

CORROSION ENVIRONMENT DIAGNOSIS SYSTEM, CORROSION PREVENTION SYSTEM, CORROSION ENVIRONMENT DIAGNOSIS METHOD, AND CORROSION PREVENTION METHOD

TECHNICAL FIELD

The present invention relates to a corrosion environment diagnosis system, a corrosion prevention system, a corrosion environment diagnosis method, and a corrosion prevention method.

BACKGROUND ART

For example, data centers in which a plurality of electronic devices are installed (telephone base stations, infrastructure facility control device machine rooms, or the like) play a role as an information infrastructure. Furthermore, due to globalization, in order to operate devices stably in countries or regions in which they are never used, it is necessary to diagnose corrosiveness of installation environments of devices in a short period of time. In emerging countries among such countries, since the emerging countries are located at low latitudes, it is estimated that relative humidity is high, and a lot of corrosive gas is emitted. According to a report by ASHRAE, in the data center, a failure that an electrode material of a chip part (a small resistor, capacitor, thermistor, or the like for surface mounting) corrodes due to reducing sulfur (for example, hydrogen sulfide) contained in corrosive gas frequently occurs.

In order to suppress corrosive damage of such electronic parts, it is desirable to diagnose corrosiveness of an installation environment, improve an air conditioning facility before a failure occurs due to corrosion of an electronic part, and replace the electronic part.

As a method of diagnosing the corrosiveness of the installation environment, in ASHRAE of NPL 1, a method of measuring a corrosion thickness of silver or copper, calculating an average corrosion progression from the corrosion thickness and an exposure period, estimating a future corrosion amount from the obtained average corrosion progression, and diagnosing the corrosiveness of the environment is employed. The corrosion thickness of silver or copper can be measured by a method of using a metal test piece exposed for one month or can be measured with high degree of accuracy by a method of using a quartz crystal microbalance (QCM) sensor or an electric resistive type sensor intended for silver or copper. In ASHRAE (NPL 1), a corrosion thickness of silver correlated with a failure of an electronic device is employed as an environment diagnostic criterion.

The method of diagnosing an environment using the corrosion thickness of silver exposed for one month is also employed in ANSI/ISA 71.04 of NPL 2 in addition to ASHRAE.

Meanwhile, in ISO-11844-1 of NPL 3, an environment is diagnosed using a corrosion thickness of silver exposed for one year. Since most environments have seasonal variations, it is desirable to diagnose an environment using an annual corrosion thickness.

For the corrosion thickness of copper, a method of formulating influence of temperature, humidity, and corrosive gas which are corrosion factors and predicting the corrosion thickness of copper as disclosed in PTLs 1 and 2 may be used.

For the corrosion thickness of silver, as disclosed by the inventors of the present invention in PTL 3, a method of formulating influence of temperature, humidity, and corrosive gas which are corrosion factors in view of seasonal variations and predicting the corrosion thickness of silver may be used. The temperature, the humidity, and the corrosive gas vary greatly depending on a season in which a test piece is exposed and vary depending on operating conditions of an electronic device as well. In this regard, PTL 3 discloses a method for predicting an annual corrosion thickness of silver with a high degree of accuracy in view of variations in the temperature and the humidity (reducing sulfur which is corrosive gas is assumed to have constant density).

On the other hand, as disclosed in NPL 4, it is clear that relative humidity dependency of silver corrosion is unknown.

In NPL 5, the inventors of the present invention have proposed a mechanism of silver corrosion by atmospheric air including a hydrogen sulfide and a nitrogen dioxide and a corrosion prediction method thereof.

CITATION LIST

Patent Literature

PTL 1: Japanese Patent Application Laid-Open No. 2012-189356
PTL 2: Japanese Patent Application Laid-Open No. 2011-58907
PTL 3: Japanese Patent Application Laid-Open No. 2010-38838

Non-Patent Literature

NPL 1: ASHRAE TC9.9, "2011 Gaseous and Particulate Contamination Guidelines For Data Centers"
NPL 2: ANSI/ISA 71.04-2013, Environmental Conditions for Process Measurement and Control Systems: Airborne Contaminants Research Triangle Park: International Society for Automation.
NPL 3: ISO 11844-1, 2006, Corrosion of Metals and Alloys-classification of Low Corrosivity Indoor Atmospheres-Part 1: Determination and Estimation of Indoor Corrosivity. Geneve, Suisse: International Organization of Standardization
NPL 4: Craig Hillman: Silver and Sulfur: Case Studies, Physics, and Possible Solusions, SMTA International Conference 2007 Proceedings
NPL 5: Minamidani: Proposal of Interpretation of Atmospheric Air Corrosion Mechanism of Silver and Corrosion Prediction Method: Material and Environment 2014 Lecture Proceedings, pp. 345-348, Published on Apr. 30, 2014

SUMMARY OF INVENTION

Technical Problem

If it is possible to predict an annual corrosion thickness of silver with a high degree of accuracy in view of variations in the temperature and the humidity (reducing sulfur which is corrosive gas is assumed to have constant density), it is possible to diagnose corrosiveness of an installation environment of a device from the annual corrosion thickness of silver.

In the corrosion diagnostic method for the installation environment disclosed in PTL 3, a prediction formula in which the corrosion of silver depends on the corrosive gas, the temperature, and the relative humidity is employed. Here, the corrosiveness of the environment was evaluated in various kinds of installation environments, and the prediction formula was found not to coincide with a measured value as a result. In other words, since the actual measurement result that the corrosion of silver does not depend on the relative humidity was obtained, the prediction formula is unable to be employed. The prediction formula has a problem in that it is difficult to predict the corrosion thickness of silver in installation environments of all electronic devices.

Further, in NPL 4, a result that the corrosion of silver depends on the relative humidity and a result that the corrosion of silver does not depend on the relative humidity are stated. The method disclosed in NFL 4 has a problem in that the dependency of the relative humidity on the corrosion thickness of silver is unclear.

In NPL 5, only the corrosion mechanism of silver by the atmospheric air including the hydrogen sulfide and the nitrogen dioxide and the corrosion prediction method thereof are proposed, but a specific configuration of estimating a future corrosion thickness is unclear.

It is an object of the present invention to accurately estimate future corrosion thickness on the basis of a corrosion mechanism by atmospheric air including corrosive gas.

Solution to Problem

The present invention includes a plurality of means to solve the above issue, and an example thereof is a corrosion environment diagnosis system including: an environment measuring device that includes a temperature sensor that measures temperature in an electronic part serving as a diagnosis target or an indoor space in which an electronic device including the electronic part is installed, a humidity sensor that measures relative humidity in the indoor space or the electronic device, a corrosion sensor that measures a corrosion thickness of the diagnosis target, and a database in which indoor environment data including the temperature and the relative humidity measured by the temperature sensor and the humidity sensor and corrosion thickness data including the corrosion thickness measured by the corrosion sensor are accumulated; an outside air environment database in which outside air environment data including previous temperature and humidity of outside air is recorded; and a diagnostic processing device capable of receiving data of the outside air environment database and the environment measuring device, wherein the diagnostic processing device decides a corrosion mechanism corresponding to a relation between the corrosion thickness and the relative humidity on the basis of the indoor environment data, the corrosion thickness data, and the outside air environment data, and estimates a future corrosion thickness of the diagnosis target.

Advantageous Effects of Invention

According to the present invention, it is possible to accurately estimate future corrosion thickness on the basis of a corrosion mechanism by atmospheric air including corrosive gas.

BRIEF DESCRIPTION OF DRAWINGS

FIG. 2 is a flowchart illustrating a process in a corrosion environment diagnosis system according to an embodiment.

FIG. 3 is a flowchart illustrating a process in an environment classifying unit 30 of FIG. 1.

FIG. 12 is a graph illustrating an example of a corrosive gas database corresponding to a geothermal power plant of FIG. 10.

FIG. 13 is a diagram illustrating contents of a corrosive gas database corresponding to a steel plant of FIG. 10.

DESCRIPTION OF EMBODIMENTS

The present invention relates to a corrosion environment diagnosis system that measures, in an indoor environment, particularly, an environment in which an electronical/electronic device is installed, a corrosion degree of corrosive gas existing in an installation environment and accurately evaluates corrosiveness of the electronical/electronic device in the installation environment over a long period of time.

Hereinafter, exemplary embodiments will be described with reference to the appended drawings.

First Embodiment

Figure 1:
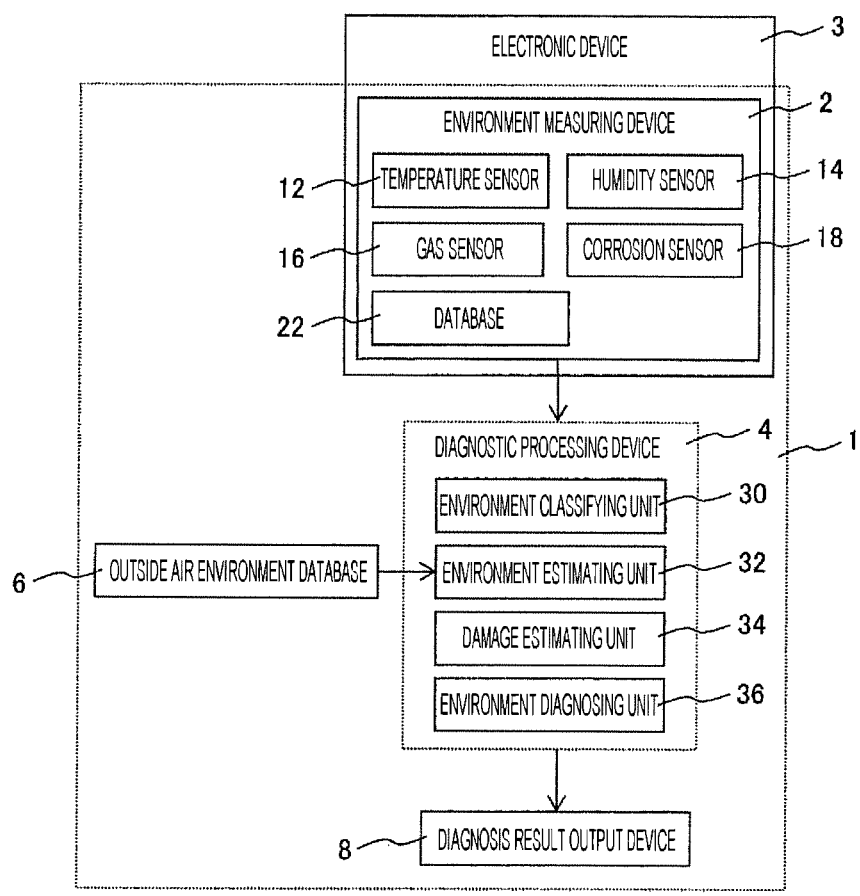
FIG. 1 is a configuration diagram illustrating a corrosion environment diagnosis system according to an embodiment of the present invention.

FIG. 1 is a block diagram of a corrosion environment diagnosis system 1.

The corrosion diagnosis system 1 includes an environment measuring device 2, a diagnostic processing device 4, an outside air environment database 6, and a diagnosis result output device 8.

The environment measuring device 2 is installed inside an electronic device 3 or an indoor space which is an environment equivalent to the inside of the electronic device 3, and an electronic part serving as a diagnosis target is installed in the electronic device 3. Here, the "indoor space" refers to the inside of a room in which the electronic device 3 is installed.

The following description will proceed with an example in which the environment measuring device 2 is installed in the electronic device 3, and an electronic part serving as a diagnosis target is installed in the electronic device 3.

The environment measuring device 2 includes a temperature sensor 12 that measures temperature in the electronic device 3 (hereinafter referred to as "inside temperature"), a humidity sensor 14 that measures relative humidity in the electronic device 3 (hereinafter referred to as "inside relative humidity"), a gas sensor 16 that measures corrosive gas density in the electronic device 3 (hereinafter referred to as "inside gas density"), a corrosion sensor 18 that measures a corrosion thickness of metal in the electronic device 3, and a database 22 that records data of the respective sensors. The temperature sensor 12, the humidity sensor 14, and the gas sensor 16 are configured to measure the inside temperature, the inside relative humidity, and the inside gas density at regular intervals and transfer data to the database 22.

Here, a controlled potential electrolytic type sensor, a semiconductor gas sensor, an electrochemical type gas sensor, or the like can be used as the gas sensor 16 that detects the hydrogen sulfide. Further, an electrochemical type gas sensor or the like can be used as the gas sensor 16 that detects the nitrogen dioxide.

The corrosion sensor 18 is preferably a high accuracy corrosion sensor having a resolution of nanometers or less such as an electric resistive type sensor or a QCM sensor. For example, the electric resistive type corrosion sensor is configured to measure a corrosion thickness at regular intervals using a principle that as a cross-sectional area of a corrosion measurement electrode on a substrate decreases due to corrosion, electric resistance increases, and transfer data to the database. Further, the QCM sensor is configured to measure a corrosion thickness at regular intervals using a principle that as a weight of a corrosion measurement electrode on a substrate increases due to corrosion, a resonance frequency decreases, and transfer data to the database 22. The corrosion sensors mentioned above are desirable because they can perform continuous measurement.

A measurement result obtained by the environment measuring device 2 is processed through the diagnostic processing device 4. The diagnostic processing device 4 is incorporated in an information processing terminal such as another electronic device (not illustrated) or a personal computer (PC).

The outside air environment database 6 stores data including a history of temperature of outside air which is outside a building in which the electronic device 3 is installed (hereinafter referred to as "outside temperature") and a history of absolute humidity outside the electronic device 3 (hereinafter referred to as "outside absolute humidity") or relative humidity outside the electronic device 3 (hereinafter referred to as "outside relative humidity"). As data of the temperature, preferably, temperature outside the electronic device 3 (in the indoor space) is stored in addition to the outside temperature and the inside temperature. In the outside air environment database 6, information of a measurement point closest to the electronic device 3 among meteorological statistical information published by a meteorological agency may be used.

As illustrated in FIG. 1, the diagnostic processing device 4 includes an environment classifying unit 30, an environment estimating unit 32, a damage estimating unit 34, and an environment diagnosing unit 36. The environment classifying unit 30 is configured to decide a corrosion mechanism occurring in the installation environment of the electronic device 3 from the measurement result obtained by the gas sensor 16 of the environment measuring device 2 and output a classified corrosion mechanism to the environment estimating unit 32. The environment estimating unit 32 is configured to estimate the inside temperature and the inside relative humidity of the electronic device 3 from the measurement result obtained by the environment measuring device 2 and the data of the outside air environment database 6 and output an estimation result to the damage estimating unit 34. The damage estimating unit 34 is configured to estimate a future corrosion thickness on the basis of the estimation result of the environment estimating unit 32 and output an estimation result to the environment diagnosing unit 36. The environment diagnosing unit 36 is configured to diagnose the corrosiveness of the environment on the basis of the corrosion mechanism classified by the environment classifying unit 30 and the estimation result of the damage estimating unit 34 and output a diagnosis result to the diagnosis result output device 8. The diagnosis result output device 8 is configured to output a diagnosis result to a display screen of an information processing terminal (not illustrated).

An operation of the corrosion environment diagnosis system 1 having the configuration will be described with reference to FIG. 2.

FIG. 2 is a process flow of the corrosion environment diagnosis system 1.

In FIG. 2, first, the environment in the electronic device 3 is measured through the temperature sensor 12, the humidity sensor 14, the gas sensor 16, and the corrosion sensor 18 installed in the environment measuring device 2 (S1). Then, the corrosion mechanism is decided through the environment classifying unit 30 of the diagnostic processing device 4 (S2). Then, the inside temperature and inside relative humidity are estimated through the environment estimating unit 32 of the diagnostic processing device 4 (S3). Then, the corrosion thickness is estimated through the damage estimating unit 34 of the diagnostic processing device 4 (S4). Then, a corrosion lifetime is diagnosed through the corrosion diagnosing unit 36 of the diagnostic processing device 4 (S5). Finally, the diagnosis result output device 8 outputs the result (S6).

In step 1 (S1), a measurement period is preferably one to three months. In the case of high-accuracy measurement, it is desirable that the measurement period be three or more months. In the case of simple measurement, the measurement period may be about one week. It is desirable that the measurement period be a period in which relative humidity having large influence on corrosive damage is high. Data measured after a scheduled measurement period is sequentially accumulated in the database 22. For example, when the measurement is performed after three or more months elapse, measured data after the measurement period is also processed through the diagnostic processing device 4, and thus the accuracy of diagnosis result is expected to be improved.

Here, as an example, silver is employed as an electrode material of the corrosion sensor to estimate the corrosion thickness. The reason is that silver more easily corrodes than copper and corrodes in a short period of time. Another reason is that in the data center, a failure that an electrode material of a chip part (a small resistor, capacitor, thermistor, or the like for surface mounting) corrodes due to reducing sulfur (for example, hydrogen sulfide) occurs, there is a correlation between the occurrence of the corrosion failure in the data center and the corrosion thickness of silver, and the corrosion thickness of silver is employed as a diagnostic criterion in ASHRAE. In ASHRAE, it is also reported that there is little correlation between the occurrence of the corrosion failure and the corrosion thickness of copper.

Step 2 (S2) will be described with reference to FIG. 3.

FIG. 3 illustrates a process of the environment classifying unit 30 of the diagnostic processing device 4.

First, when hydrogen sulfide density $[H_2S]$ and nitrogen dioxide density $[NO_2]$ are measured through the gas sensor 16, a corrosion mechanism is decided in accordance with a ratio of the measured hydrogen sulfide density and the measured nitrogen dioxide density, and a corrosion rate based on the corrosion mechanism is calculated.

The inventors of the present invention found that the corrosion mechanism of silver depends on the ratio of the hydrogen sulfide density and the nitrogen dioxide density, and the dependency of the relative humidity on the corrosion changes in accordance with the ratio, and the corrosion rate of each corrosion mechanism was formulated (NPL 5). The ratio of the hydrogen sulfide density and the nitrogen dioxide density is classified into (1) a case in which the hydrogen sulfide density is higher than ½ of the nitrogen dioxide density, (2) a case in which the hydrogen sulfide density is ½ of the nitrogen dioxide density, and (3) a case in which the hydrogen sulfide density is less than ½ of the nitrogen dioxide density. The details will be described below with reference to FIG. 4.

Figure 4:
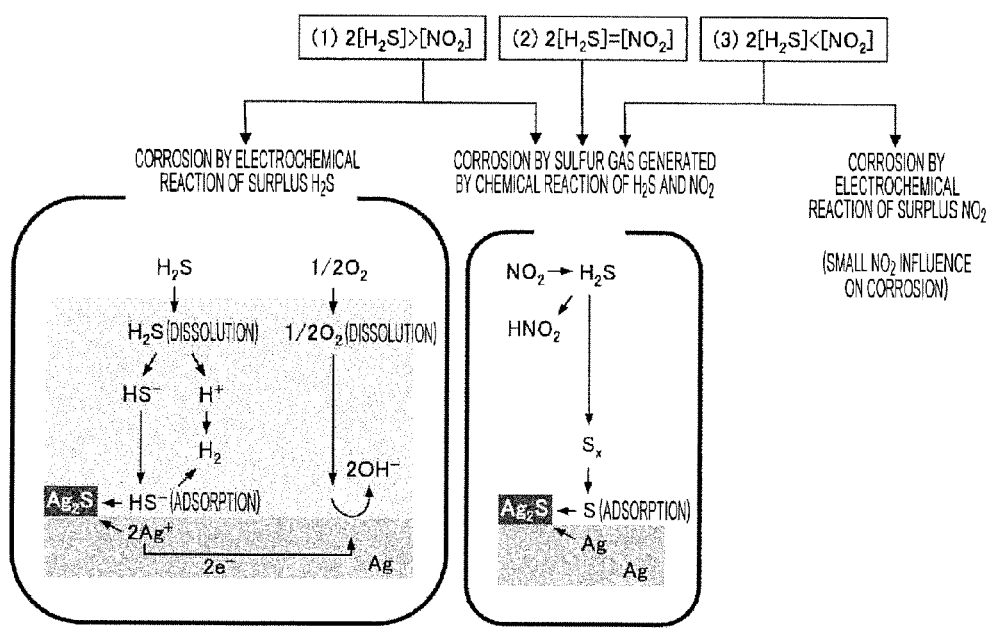
FIG. 4 is a conceptual diagram illustrating classification of a corrosion mechanism of $H_2S$—$NO_2$-based silver.

FIG. 4 illustrates the corrosion mechanism in addition to the above case classification.

(1) Case in which the Hydrogen Sulfide Density is Higher than ½ of the Nitrogen Dioxide Density $(2[H_2S]>[NO_2])$ A corrosion mechanism in a case in which the hydrogen sulfide density is higher than ½ of the nitrogen dioxide density is a corrosion reaction in which corrosion that does not depend on the relative humidity by sulfur gas produced by a chemical reaction between a part of the hydrogen sulfide and the entire nitrogen dioxide and a corrosion that depends on the relative humidity by a surplus hydrogen sulfide having high corrosiveness overlap each other.

The hydrogen sulfide is dissolved in a water film formed on a metal surface and dissociated into $HS^-$. Further, $HS^-$ is adsorbed to a silver surface and combined with anode-dissolved $Ag^+$ to produce $Ag_2S$. A cathode reaction is a reduction reaction of dissolved oxygen ($\frac{1}{2}O_2+H_2O+2e^-=2OH^-$) or a reduction reaction of $NO_3^-$ ($NO_3^-+4H^++3e^-=NO+H_2O$) produced by dissolution of $NO_2$ gas. Therefore, in a high humidity environment in which a water film is formed, an electrochemical reaction by the surplus hydrogen sulfide dissolved in the water film depends on the relative humidity. For this reason, a reaction depending on the relative humidity by the surplus hydrogen sulfide becomes dominant in the entire corrosion, and thus the corrosion rate depends on the relative humidity.

(2) Case in which the Hydrogen Sulfide Density is ½ of the Nitrogen Dioxide Density $(2[H_2S]=[NO_2])$ In a corrosion mechanism in a case in which the hydrogen sulfide density is ½ of the nitrogen dioxide density, corrosion by the sulfur gas produced by the chemical reaction of the entire hydrogen sulfide and the entire nitrogen dioxide is main corrosion, and the corrosion rate does not depend on the relative humidity.

(3) Case in which the Hydrogen Sulfide Density is Less than ½ of the Nitrogen Dioxide Density $(2[H_2S]<[NO_2])$ In a corrosion mechanism in a case in which the hydrogen sulfide density is less than ½ of the nitrogen dioxide density, corrosion by the sulfur gas produced by the chemical reaction $(8H_2S+16NO_2=S_8+16HNO_2)$ between the entire hydrogen sulfide and a part of the nitrogen dioxide is main corrosion. The corrosion of silver $(16\,Ag+S_8=8Ag_2S)$ by the produced sulfur gas $S_8$ does not depend on the relative humidity, and the sulfur gas $S_8$ has stronger corrosiveness for silver than $H_2S$ having the same density. In addition, the corrosion by the electrochemical reaction by the surplus nitrogen dioxide progresses in parallel. In the high humidity environment in which the water film is formed, the electrochemical reaction by the nitrogen dioxide dissolved in the water film depends on the relative humidity, but the corrosiveness is remarkably weaker than that in the corrosion reaction by the hydrogen sulfide or the sulfur gas. For this reason, in terms of the entire corrosion, the corrosion by the sulfur gas is main corrosion, and the corrosion rate does not depend on the relative humidity.

As described above, in the process of the environment classifying unit 30 of the diagnostic processing device 4, the ratio of the hydrogen sulfide density and the nitrogen dioxide density is classified into (1) a case in which the hydrogen sulfide density is higher than ½ of the nitrogen dioxide density, (2) a case in which the hydrogen sulfide density is ½ of the nitrogen dioxide density, and (3) a case in which the hydrogen sulfide density is less than ½ of the nitrogen dioxide density, and the corrosion mechanism of each case is decided. $SO_2$ existing in the atmospheric air does not influence the corrosion of silver and thus is excluded here.

Step 3 (S3) will be described with reference to FIG. 5.

Figure 5:
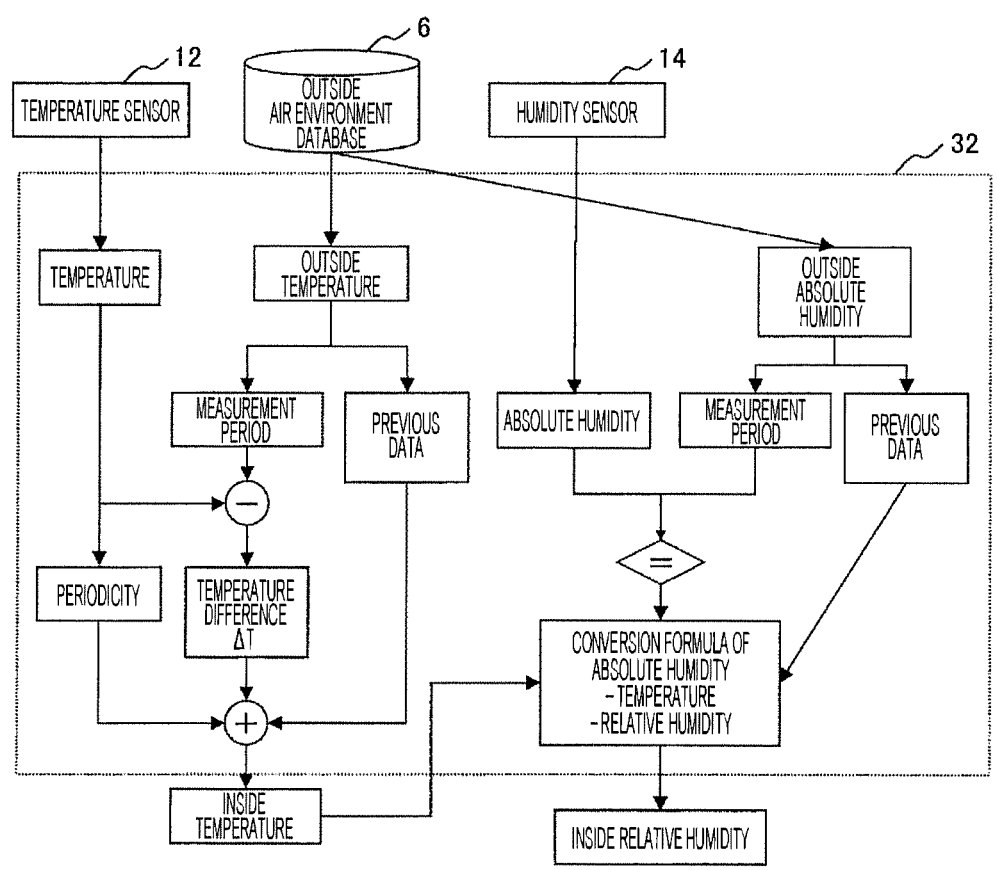
FIG. 5 is a flowchart illustrating a process in an environment estimating unit 32 of FIG. 1.

FIG. 5 illustrates a process of the environment estimating unit 32 of the diagnostic processing device 4.

In FIG. 5, as input information of the environment estimating unit 32, there is data from the temperature sensor 12, the humidity sensor 14, and the outside air environment database 6.

First, for the temperature, a temperature difference $\Delta T$ between the inside temperature and the outside temperature is calculated. For example, the temperature difference $\Delta T$ is obtained from an average value of the temperature differences $\Delta T$ between the inside temperature and the outside temperature for one to three months. Further, a frequency characteristic of the inside temperature is extracted through discrete Fourier analysis. The inside temperature is influenced by the outside temperature and heat produced by an operation of the electronic device. For example, the inside temperature of the electronic device 3 that operates and stops everyday has a characteristic of a one-day cycle due to the operation and the stoppage in addition to a variation in the outside temperature. In the electronic device 3 that operates and stops on weekdays and stops at weekends has a characteristic of a one-week cycle in addition to a characteristic of a one-day cycle. Typically, the electronic device 3 has hardly a characteristic of a period exceeding one week, but it is possible to acquire a frequency characteristic of any cycle through Fourier analysis.

It is possible to estimate future inside temperature by applying the calculated temperature difference $\Delta T$ and the frequency characteristics to previous outside temperature before the measurement period in which the obtained frequency characteristic is stored in the outside air environment database 6.

Next, the estimation of the inside relative humidity will be described.

Since moisture (absolute humidity) outside the electronic device 3 immediately moves into the electronic device 3, the outside absolute humidity and the inside absolute humidity substantially coincide with each other. Therefore, if it is possible to compare the outside absolute humidity obtained from the outside air environment database with the inside absolute humidity calculated using the measured inside temperature and the inside relative humidity and confirm that the outside absolute humidity is equal to the inside absolute humidity, it is possible to estimate the future inside relative humidity from the previous outside absolute humidity using an absolute humidity-temperature-relative humidity conversion formula (for example, D. Sonntag, Z. Meteorol. 70, 340, 1990).

As described above, in the environment measuring unit 32, a correspondence relation between the outside temperature and the outside absolute humidity and the inside temperature and the inside relative humidity in the same period as the measurement period is obtained, and it is possible to estimate the future inside temperature and the future inside relative humidity on the basis of the correspondence relation and the previous outside temperature and the previous outside absolute humidity.

A corrosion-related process of the damage estimating unit 34 in step 4 (S4) will be described with reference to FIG. 6.

Figure 6:
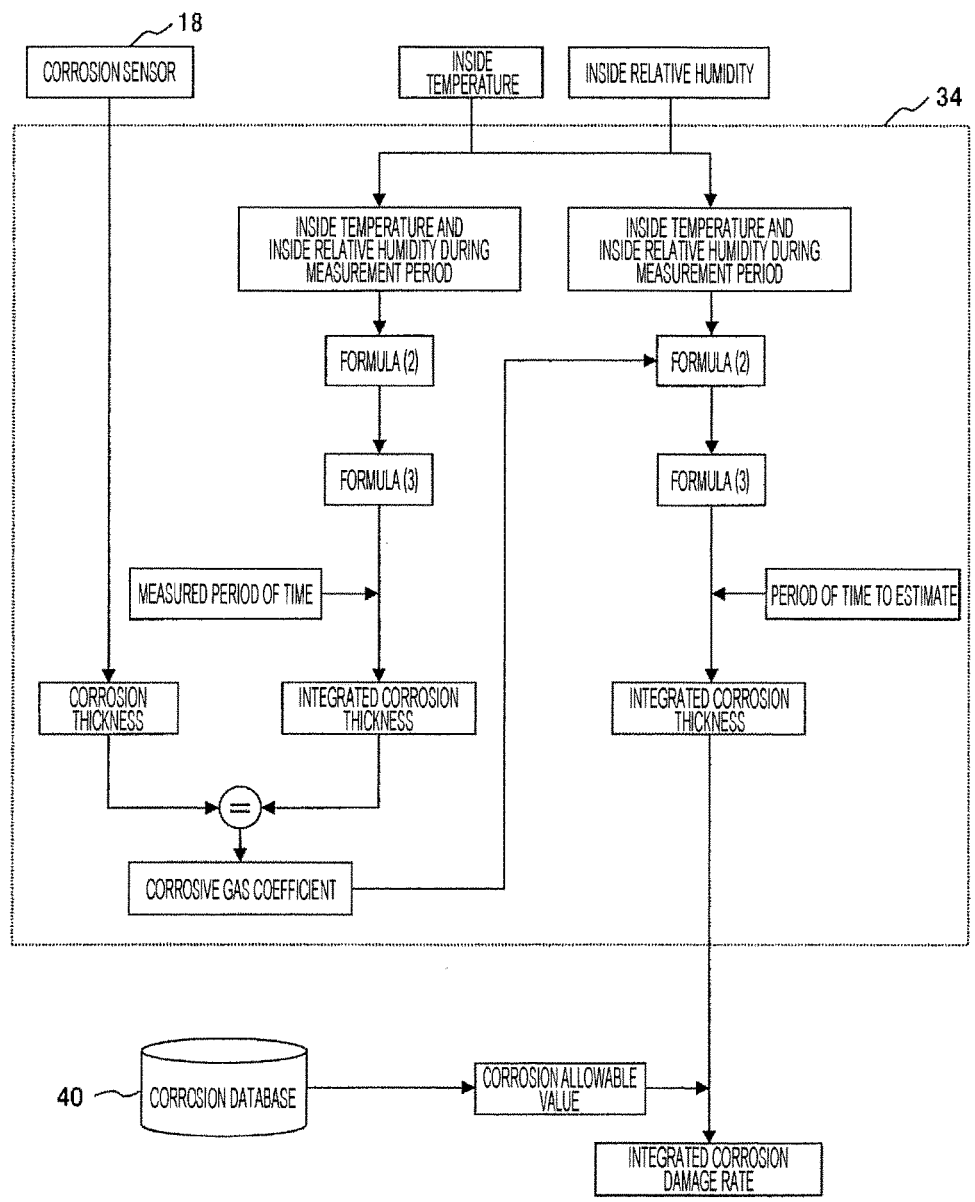
FIG. 6 is a flowchart illustrating a process of estimating a corrosion thickness in a damage estimating unit 34 of FIG. 1.

FIG. 6 illustrates a process of the damage estimating unit 34. The corrosion thickness measured in step 1 (S1), the corrosion mechanism decided in step 2 (S2), and the inside temperature and the inside relative humidity estimated in step 3 (S3) are input to the damage estimating unit 34.

Then, a correlation between the inside temperature and the inside relative humidity and the corrosion thickness is obtained. In step 2 (S2), the ratio of the hydrogen sulfide density and the nitrogen dioxide density is classified into (1) a case in which the hydrogen sulfide density is higher than ½ of the nitrogen dioxide density, (2) a case in which the hydrogen sulfide density is ½ of the nitrogen dioxide density, and (3) a case in which the hydrogen sulfide density is less than ½ of the nitrogen dioxide density, and the corrosion mechanism of each case is decided. A result of summarizing the corrosion mechanism of $H_2S-NO_2$-based silver is described.

(a) $H_2S$ is oxidized by $NO_2$ to produce $S_8$. Silver produces a silver sulfide by $S_8$. A sulfidation reaction by $S_8$ does not depend on the relative humidity.

(b) In a case in which the $H_2S$ density is higher than ½ of $NO_2$ density, $NO_2$ is entirely consumed by a chemical reaction, but $H_2S$ is surplus. On the other hand, when the $H_2S$ density is higher than ½, $NO_2$ is surplus.

(c) The surplus $H_2S$ or $NO_2$ depends on the relative humidity and is dissolved in the water film formed on the silver surface. The dissolved $H_2S$ or $NO_2$ contributes to the electrochemical reaction and promotes the corrosion of silver.

(d) $SO_2$ does not influence the corrosion of silver.

The inventors of the present invention formulated the corrosion rate of each corrosion mechanism on the basis of the corrosion mechanism which is found out here using experimental formulas to be described below.

(1) In a case in which the hydrogen sulfide density is higher than ½ of the nitrogen dioxide density, a corrosion thickness X (nm) is indicated by the following Formula (1).

$$X = \{A[H_2S]_{chem} + B[H_2S]_{e\text{-}chem}^n \cdot \exp(C \cdot RH) \cdot \exp(-E/RT)\} \cdot t \quad (1)$$

Here, A, B, and C are coefficients, n is an exponent, $[H_2S]_{chem}$ is density of $H_2S$ that reacts with $NO_2$, $[H_2S]_{e\text{-}chem}$ is density of surplus $H_2S$, T is temperature, RH is relative humidity, E is activation energy, R is gas constant, and t is time.

Then, an approximation formula of the corrosion thickness (nm) is reviewed.

Since the corrosion thickness X of silver is proportional to a time, a corrosion thickness $X_{CS}$ in a measurement period $t_{CS}$ of the corrosion sensor 18 is obtained by the following Formula (2) as an integrated value of a corrosion thickness $X_{UT}$ of a unit time $t_{UT}$.

$$X_{CS} = \Sigma X_{UT} = A[H_2S]_{chem} \Sigma\{t_{UT}\} + B[H_2S]_{e\text{-}chem}^n \cdot \Sigma\{\exp(C \cdot RH) \cdot \exp(-E/RT) \cdot t_{UT}\} \quad (2)$$

Here, since the temperature and the relative humidity are estimated by the environment estimating unit 32, a term of $B[H_2S]_{e\text{-}chem}^n \cdot \Sigma E \{\exp(C \cdot RH) \cdot \exp(-E/RT) \cdot t_{UT}\}$ of Formula (2) is considered to have a variation. In this regard, a coefficient $B[H_2S]_{e\text{-}chem}^n$ may be estimated using environment data instead of a fixed value as indicated in the following Formula (3).

$$B[H_2S]_{e\text{-}chem}^n = [X_{CS} - A[H_2S]_{chem} \Sigma\{t_{UT}\}]/\Sigma\{\exp(C \cdot RH) \cdot \exp(-E/RT) \cdot t_{UT}\} \quad (3)$$

As described above, the corrosive gas coefficient $B[H_2S]_{e\text{-}chem}^n$ is a unique value for each installation environment and can be decided by substituting the inside temperature, the inside relative humidity, and the corrosion thickness measured by Formula (3) and the measurement period.

Formula (1) can be simply indicated by the following Formula (4).

$$X = B'[H_2S] \cdot \exp(C' \cdot RH) \cdot \exp(-E/RT) \cdot t \quad (4)$$

Here, B' and C' are coefficients. The corrosion thickness $X_{UT}$ at the measurement unit time $t_{UT}$ of each sensor of the environment measuring device 2 is indicated by the following Formula (5) in an environment of the temperature T and the relative humidity RH.

$$X_{UT} = B'[H_2S] \cdot \exp(C' \cdot RH) \cdot \exp(-E/RT) \cdot t_{UT} \quad (5)$$

Since the corrosion thickness X of silver is proportional to a time, the corrosion thickness $X_{CS}$ in the measurement period $t_{CS}$ of the corrosion sensor 18 is indicated by the following Formula (6) as an integrated value of a corrosion amount of the unit time $t_{UT}$.

$$X_{CS}=\Sigma X_{UT}=B'[H_2S]\cdot\Sigma\{\exp(C'\cdot RH)\cdot\exp(-E/RT)\cdot t_{UT}\} \quad (6)$$

B'[H$_2$S] is indicated by the following Formula (7) on the basis of Formula (6).

$$B'[H_2S]=X_{CS}/\Sigma\{\exp(C'\cdot RH)\cdot\exp(-E/RT)\cdot t_{UT}\} \quad (7)$$

Thus, the corrosive gas coefficient B'[H$_2$S] is a unique value for each installation environment and decided by substituting the inside temperature, the inside relative humidity, and the corrosion thickness measured by Formula (5) and the measurement period.

When the estimation is actually performed by using a computer, a method of setting the corrosive gas coefficient so that an integrated corrosion thickness estimated by assuming a provisional corrosive gas coefficient in advance is equal to the corrosion thickness $X_{CS}$ in the measurement period $t_{CS}$ of the corrosion sensor 18 may be employed. Here, the seasonal variation of the corrosive gas coefficient is not considered, but the estimation can be performed with a higher degree of accuracy when the seasonal variation of the corrosive gas coefficient measured in a certain period is considered. It is possible to estimate the integrated corrosion thickness by substituting the decided corrosive gas coefficient and the values of the inside temperature and the inside relative humidity estimated in step 3 (S3) into Formula (2) or (6).

(2) Case in which the hydrogen sulfide density is ½ of the nitrogen dioxide density and (3) case in which the hydrogen sulfide density is less than ½ of the nitrogen dioxide density In a corrosion mechanism in cases in which the hydrogen sulfide density is ½ of the nitrogen dioxide density and less than ½ of the nitrogen dioxide density, corrosion by the sulfur gas produced by the chemical reaction of the entire hydrogen sulfide and the entire nitrogen dioxide is main corrosion, and the corrosion rate does not depend on the relative humidity. The corrosion thickness X (nm) is indicated by the following Formula (8).

$$X=D[H_2S]_{chem}\cdot t \quad (8)$$

Here, D indicates a coefficient, [H$_2$S]$_{chem}$ indicates density of H$_2$S which reacts with NO$_2$. The corrosion thickness has no dependency on the relative humidity, and the dependency on the temperature is small and ignorable. Since the corrosion thickness X of silver is proportional to a time, the corrosion thickness $X_{CS}$ in the measurement period $t_{CS}$ of the corrosion sensor 18 is indicated by the following Formula (9).

$$X_{CS}=D[H_2S]_{chem}\cdot t_{UT} \quad (9)$$

D[H$_2$S]$_{chem}$ is indicated by the following Formula (10) on the basis of Formula (9).

$$D[H_2S]_{chem}=X_{CS}/t_{UT} \quad (10)$$

As described above, the corrosive gas coefficient D[H$_2$S]$_{chem}$ is a unique value for each installation environment of the electronic device and can be decided by substituting the corrosion thickness measured by Formula (9) and the measurement period.

In step 5 (S5), a ratio of the corrosion thickness estimated in step 4 (S4) and a corrosion allowable value stored in a corrosion database 40 is input to the corrosion diagnosing unit 36. The corrosion diagnosing unit 36 obtains an integrated corrosive damage rate from the ratio, and obtains a point in time at which the integrated corrosive damage rate reaches one as a corrosion lifespan. If there is no corrosion allowable value in the corrosion database 40, it is possible to classify corrosiveness of an environment, for example, on the basis of a corrosion amount of metal stated in ISO 11844-1 and perform the diagnosis.

Second Embodiment

Step 2 (S2) of a corrosion environment diagnosis system 1 according to a second embodiment "decision of the corrosion mechanism by the environment classifying unit 30" will be described with reference to FIG. 7.

Figure 7:
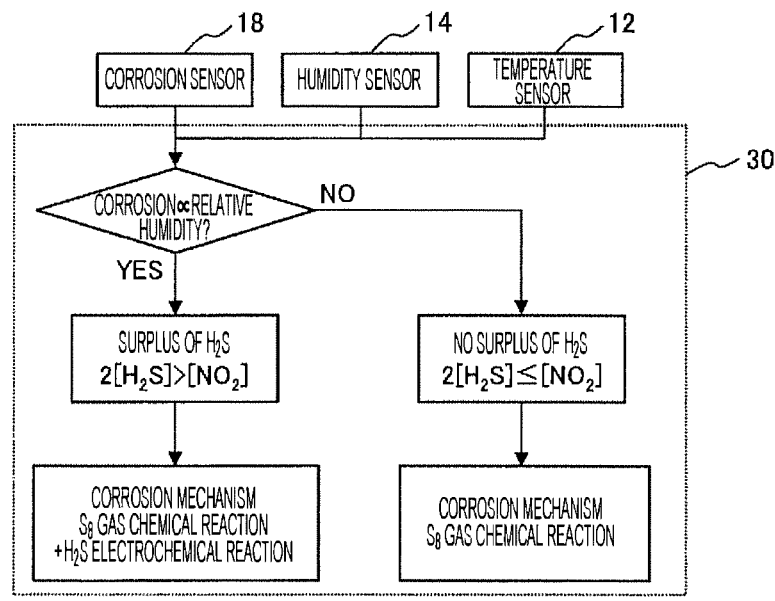
FIG. 7 is a flowchart illustrating another example of the process in the environment classifying unit 30 of FIG. 1.

FIG. 7 illustrates a process of the environment classifying unit 30 of the diagnostic processing device 4.

In the first embodiment, the hydrogen sulfide density and the nitrogen dioxide density are measured through the gas sensor 16, the corrosion mechanism depending on the ratio of the hydrogen sulfide density and the nitrogen dioxide density is decided, and the corrosion rate based on the corrosion mechanism is further obtained.

On the other hand, in the present embodiment, the corrosion mechanism is decided from a degree of relative humidity dependency of corrosion thickness data using indoor humidity data and corrosion thickness data which are recorded in a set period through corrosion sensor 18, the temperature sensor 12, and the humidity sensor 14. By investigating the presence or absence of the relative humidity dependency of the corrosion thickness data, it is possible to classify the environment into (1) a case in which the hydrogen sulfide density is higher than ½ of the nitrogen dioxide density, (2) a case in which the hydrogen sulfide density is ½ of the nitrogen dioxide density, and (3) a case in which the hydrogen sulfide density is less than ½ of the nitrogen dioxide density without using the gas sensor 16.

When the corrosion thickness data in the target environment depends on the relative humidity, it corresponds to (1) a case in which the hydrogen sulfide density is higher than ½ of the nitrogen dioxide density. On the other hand, when the corrosion thickness data in the target environment does not depend on the relative humidity, it corresponds to (2) a case in which the hydrogen sulfide density is ½ of the nitrogen dioxide density or (3) a case in which the hydrogen sulfide density is less than ½ of the nitrogen dioxide density.

(1) In a case in which the hydrogen sulfide density is higher than ½ of the nitrogen dioxide density, Formulas (4) to (7) indicated as the simple relational expressions in the first embodiment are employed as the corrosion thickness X (nm). Here, the integrated corrosion thickness is accurately estimated by substituting the values of the inside temperature and the inside relative humidity estimated in step 3 (S3) and the decided corrosive gas coefficient into Formula (6).

(2) In cases in which the hydrogen sulfide density is ½ of the nitrogen dioxide density and less than ½ of the nitrogen dioxide density, Formulas (8) to (10) indicated as the simple relational expressions in the first embodiment are employed as the corrosion thickness X (nm). Here, the integrated corrosion thickness is accurately estimated by substituting the decided corrosive gas coefficient into Formula (9).

In step 5 (S5), the ratio of the corrosion thickness estimated in step 4 (S4) and the corrosion allowable value stored in the corrosion database 40 is input to the corrosion diagnosing unit 36. The corrosion diagnosing unit 36 obtains the integrated corrosive damage rate from the ratio and obtains a point in time at which the integrated corrosive damage rate reaches one as the corrosion lifespan. If there is no corrosion allowable value in the corrosion database 40, it is possible to classify corrosiveness of an environment, for example, on the basis of a corrosion amount of metal stated in ISO 11844-1 and perform the diagnosis.

Figure 8A:
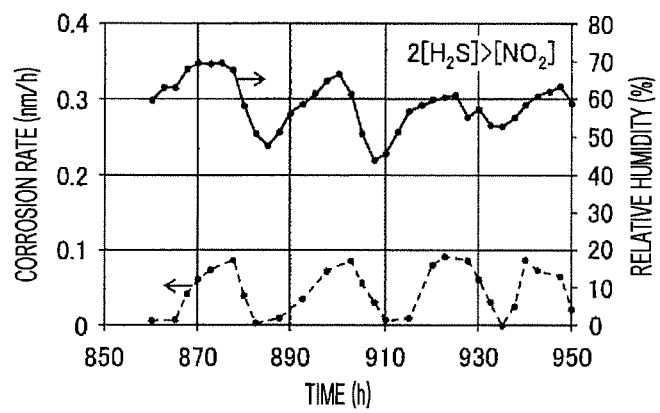
FIG. 8A is a graph illustrating a temporal change when a corrosion rate depends on relative humidity under a condition that there is a large amount of hydrogen sulfide.

FIG. 8A is a graph illustrating a temporal change when the corrosion rate depends on the relative humidity under the condition that there is a large amount of hydrogen sulfide. Here, the corrosion rate is an amount of change in the corrosion thickness per unit time.

As illustrated in FIG. 8A, for example, when the relative humidity change and the corrosion thickness are investigated for one day, the corrosion thickness tends to increase with the increase in the relative humidity. When this characteristic is obtained, it is classified into (1) a case in which the hydrogen sulfide density is higher than ½ of the nitrogen dioxide density. It is understood from FIG. 8A that the corrosion rate tends to increase when the relative humidity is approximately 60% or more, and the corrosion rate tends to decrease when the relative humidity is less than 60%. Therefore, in order to suppress the progression of corrosion, it is desirable to reduce the relative humidity to be 60% or less.

On the other hand, when the corrosion thickness does not change with the increase in the relative humidity, the environment can be classified into (2) a case in which the hydrogen sulfide density is ½ of the nitrogen dioxide density or (3) a case in which the hydrogen sulfide density is less than ½ of the nitrogen dioxide density.

Figure 8B:
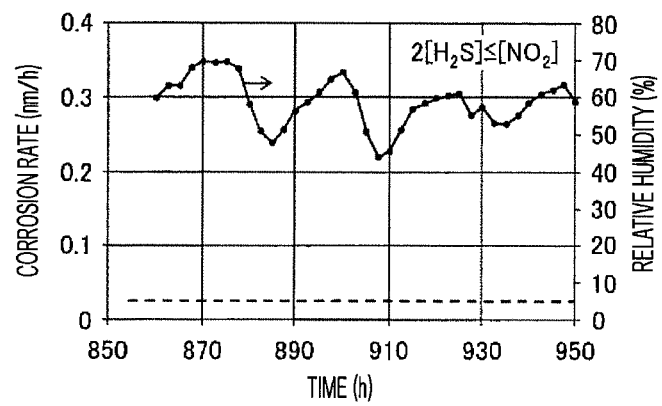
FIG. 8B is a graph illustrating a temporal change when a corrosion rate does not depend on relative humidity under a condition that there is a small amount of hydrogen sulfide.

FIG. 8B illustrates this state and is a graph illustrating a temporal change when the corrosion rate does not depend on the relative humidity under the condition that there is a small amount of hydrogen sulfide.

As illustrated in FIG. 8B, the corrosion rate is constant regardless of the relative humidity.

FIGS. 8A and 8B correspond to the illustration of FIG. 4 and the description thereof.

Third Embodiment

In step 2 (S2) of a corrosion environment diagnosis system 1 according to a third embodiment "decision of the corrosion mechanism by the environment classifying unit 30," the ratio of the hydrogen sulfide density and the nitrogen dioxide density is classified into (1) a case in which the hydrogen sulfide density is higher than ½ of the nitrogen dioxide density, (2) a case in which the hydrogen sulfide density is ½ of the nitrogen dioxide density, and (3) a case in which the hydrogen sulfide density is less than ½ of the nitrogen dioxide density, and the corrosion mechanism of each case is decided. The inventors of the present invention formulated the corrosion rate for each corrosion mechanism using experimental formulas to be described below.

(1) In a case in which the hydrogen sulfide density is higher than ½ of the nitrogen dioxide density, the corrosion thickness X (nm) is indicated by Formula (11).

$$X=13.8[H_2S]_{chem}+\exp(30.94)\cdot[H_2S]_{e\text{-}chem}^{0.41}\cdot\exp(4.47\cdot RH/100)\cdot\exp(-83100/RT)\cdot t \quad (11)$$

Here, $[H_2S]_{e\text{-}chem}$ indicates density of $H_2S$ that reacts with $NO_2$, $[H_2S]_2$ indicates density of surplus $H_2S$, T is temperature, RH is relative humidity, and R is a gas constant.

(2) Case in which the hydrogen sulfide density is ½ of the nitrogen dioxide density and (3) case in which the hydrogen sulfide density is less than ½ of the nitrogen dioxide density In a corrosion mechanism in cases in which the hydrogen sulfide density is ½ of the nitrogen dioxide density and less than ½ of the nitrogen dioxide density, corrosion by the sulfur gas produced by the chemical reaction of the entire hydrogen sulfide and the entire nitrogen dioxide is main corrosion, and the corrosion rate does not depend on the relative humidity. The corrosion thickness X (nm) is indicated by Formula (12).

$$X=13.8[H_2S]_{chem}\cdot t \quad (12)$$

Formulas (11) and (12) are experimental formulas obtained from data of 55 cases of Rice (J. Electrochem. Soc., 128, 275, 1981), 7 cases of Abbott (IEEE Trans. Parts, Hybrids, and Packaging PHP— 10, 24, 1974), 10 cases of Hiramoto (Material life, 11, 109, 1999), ad 38 cases of Shiga (Furukawa review, 76-11, 93, 1985).

Modified Example

Figure 9:
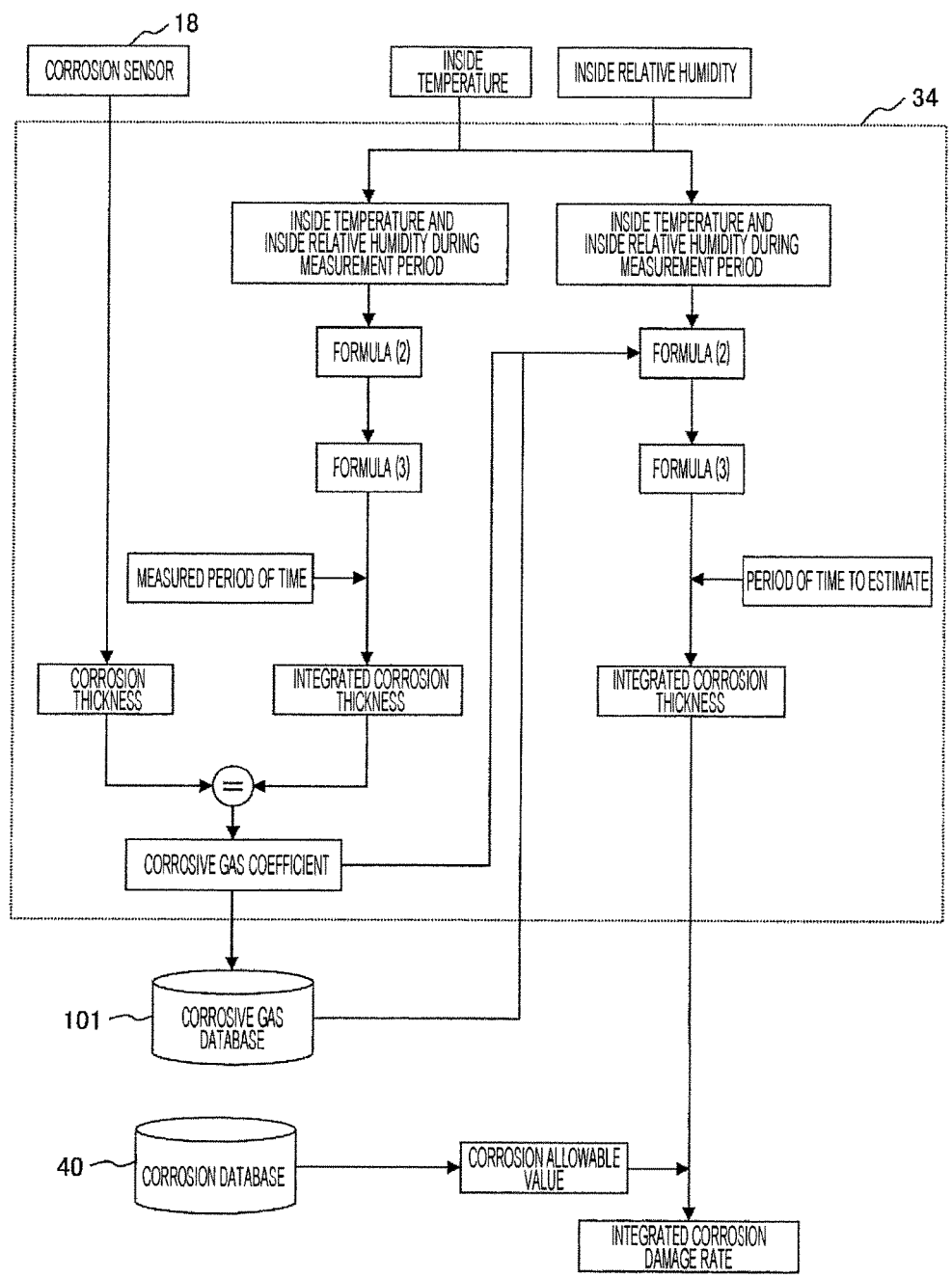
FIG. 9 is a flowchart illustrating a modified example of FIG. 6.

FIG. 9 is a flowchart illustrating a modified example of FIG. 6.

In FIG. 9, the corrosive gas coefficient obtained from a sum of the corrosion thickness and the integrated corrosion thickness is recorded and accumulated in a corrosive gas database 101.

Figure 10:
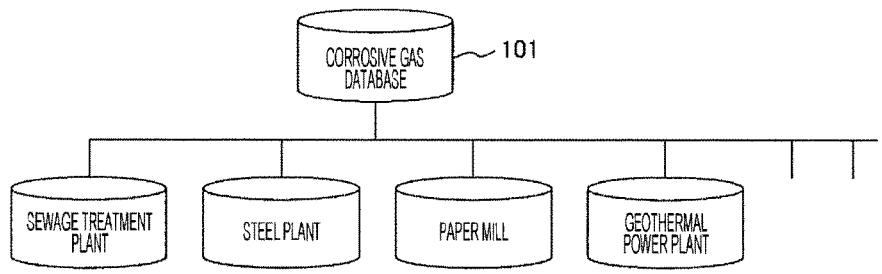
FIG. 10 is an overall configuration diagram illustrating a corrosive gas database corresponding to a facility having various kinds of environments.

FIG. 10 is an overall configuration diagram illustrating the corrosive gas database corresponding to a facility having various kinds of environments.

The corrosive gas database 101 illustrated in FIG. 10 indicates a concept of a database based on cloud computing (cloud).

Figure 11:
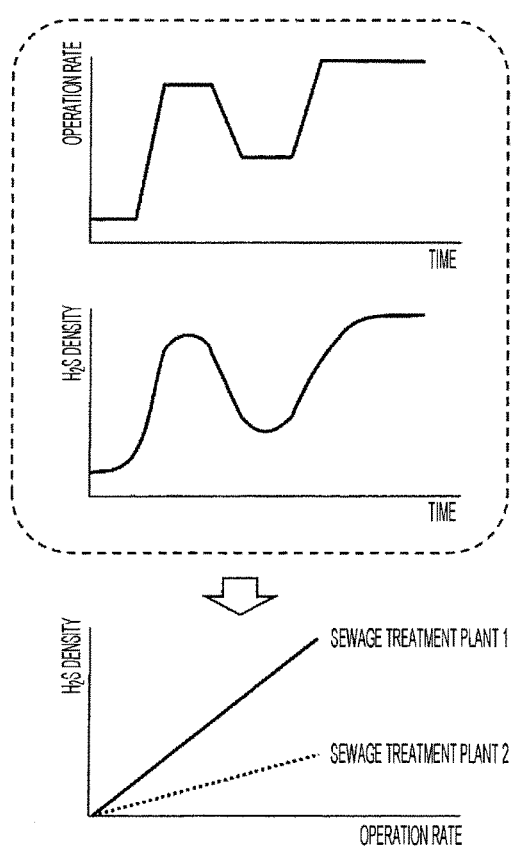
FIG. 11 is a graph illustrating an example of a corrosive gas database corresponding to a sewage treatment plant of FIG. 10.

FIG. 11 is a graph illustrating an example of the corrosive gas database corresponding to a sewage treatment plant of FIG. 10.

FIG. 11 illustrates a process of plotting a relation (a sewage treatment plant 1) between an operation rate and the hydrogen sulfide density at each time from the operation rate of the sewage treatment plant and the temporal change in the hydrogen sulfide density (the $H_2S$ density) at a predetermined position near the sewage treatment plant on a graph. Here, a straight line indicated by a dotted line is an example of a sewage treatment plant 2 having relatively low hydrogen sulfide density. In both cases, the operation rate and the hydrogen sulfide density have a direct proportional relation.

FIG. 12 is a graph illustrating an example of the corrosive gas database corresponding to a geothermal power plant of FIG. 10.

FIG. 12 illustrates a process of plotting a relation (a geothermal power plant 1) between the operation rate and the hydrogen sulfide density at each time on a graph in a similar manner to that of FIG. 11. A straight line illustrated by a dotted line is an example of a geothermal power plant 2, which has a relatively low hydrogen sulfide density. In both cases, the operation rate and the hydrogen sulfide density have a relation expressed by a linear function, but even when the operation rate is 0, the hydrogen sulfide density is not 0. This is because, in the case of the geothermal power plant, a hot spring or a volcano is likely to be located nearby, and the hydrogen sulfide continues to be produced from the surrounding area regardless of the operation of the facility.

FIG. 13 is a diagram illustrating content of the corrosive gas database corresponding to a steel plant of FIG. 10.

In FIG. 13, data classified as structure data, environment data, and operation data is stored as the corrosive gas database.

Figure 14:
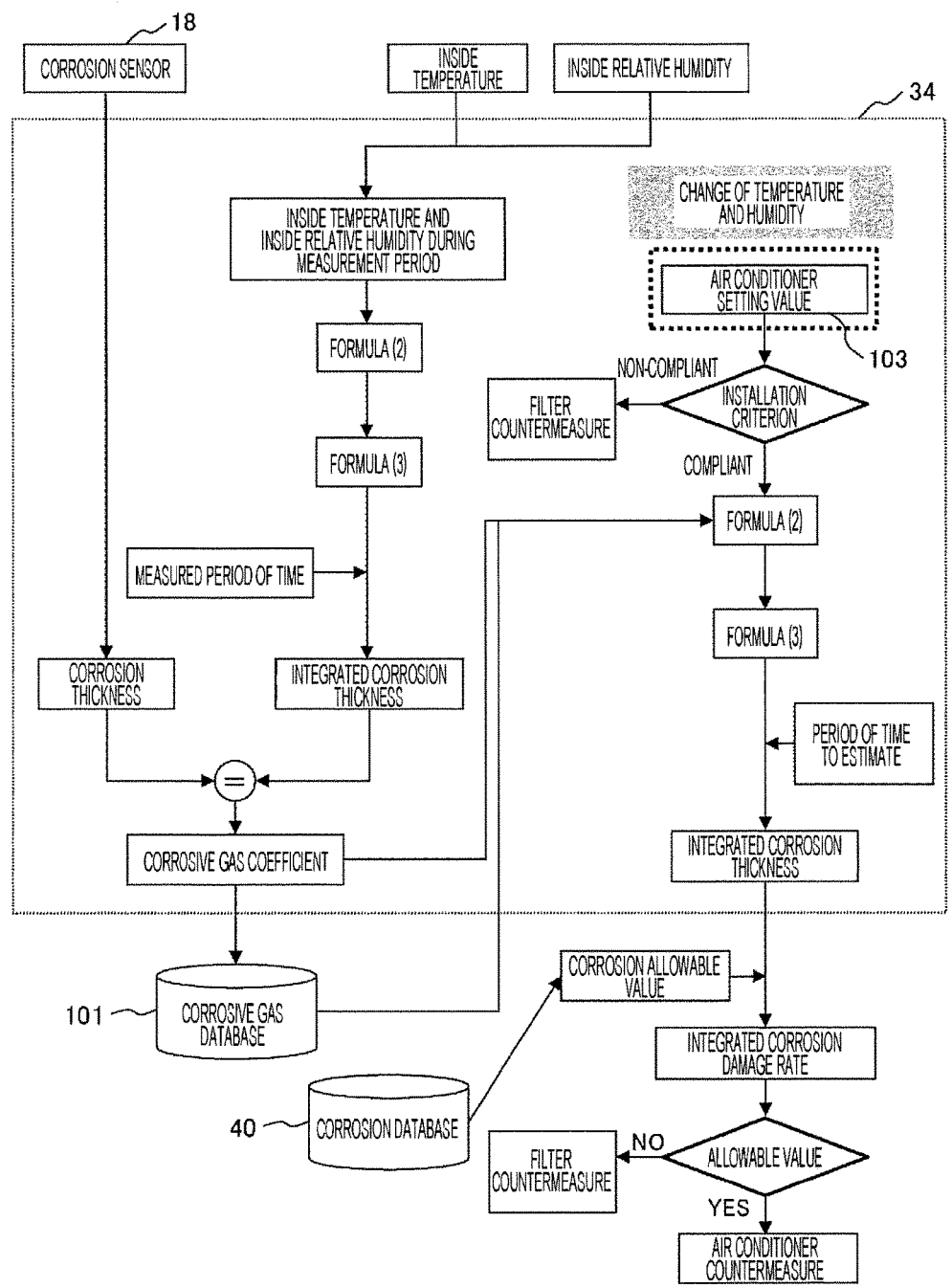
FIG. 14 is a flowchart illustrating an anticorrosion method according to the present invention.

FIG. 14 is a flowchart illustrating a corrosion prevention method according to the present invention.

In FIG. 14, corrosion of metal in an electronic device is suppressed by controlling temperature and humidity in a room (indoor space) in which the electronic device is installed.

Specifically, an air conditioning device (air conditioner) that adjusts the temperature and the humidity of the room in which the electronic device is installed is used, an air conditioner setting value 103 used for suppressing corrosion of metal is input, and it is determined whether or not the air conditioner setting value 103 is compliant with an installation criterion (an air conditioner control allowable range). When the air conditioner setting value 103 is not compliant, a countermeasure such as removal of the corrosive gas by the filter is reviewed.

On the other hand, when the air conditioner setting value 103 is compliant with the installation criterion, the integrated corrosion thickness is calculated using the calculated corrosive gas coefficient or data in the corrosive gas database 101, and then the integrated corrosive damage rate is calculated. Then, the integrated corrosive damage rate is compared with an allowable value, and it is determined whether or not it is sufficiently controlled only by control of the air conditioner. When it is not sufficiently controlled only by control of the air conditioner, a countermeasure such as removal of the corrosive gas by the filter is executed. Here, data of ISO 11844-1 may be used as the allowable value used as the determination criterion. Further, the countermeasure by the filter is mainly removal of the hydrogen sulfide. In addition to this, it is desirable to remove the nitrogen dioxide as well.

Figure 15:
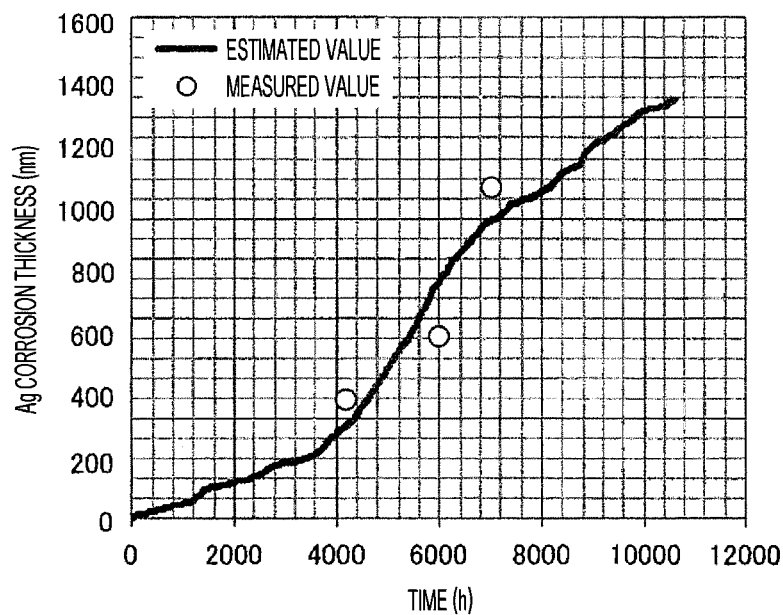
FIG. 15 is a graph illustrating an example of a temporal change in a corrosion thickness of $H_2S$—$NO_2$-based silver.

FIG. 15 is a graph illustrating an example of a temporal change in the corrosion thickness of $H_2S$—$NO_2$-based silver. An estimated value calculated by the method of the present invention and a measured value are illustrated together.

It is understood from FIG. 15 that the estimated value and the measured value substantially coincide with each other.

Figure 16:
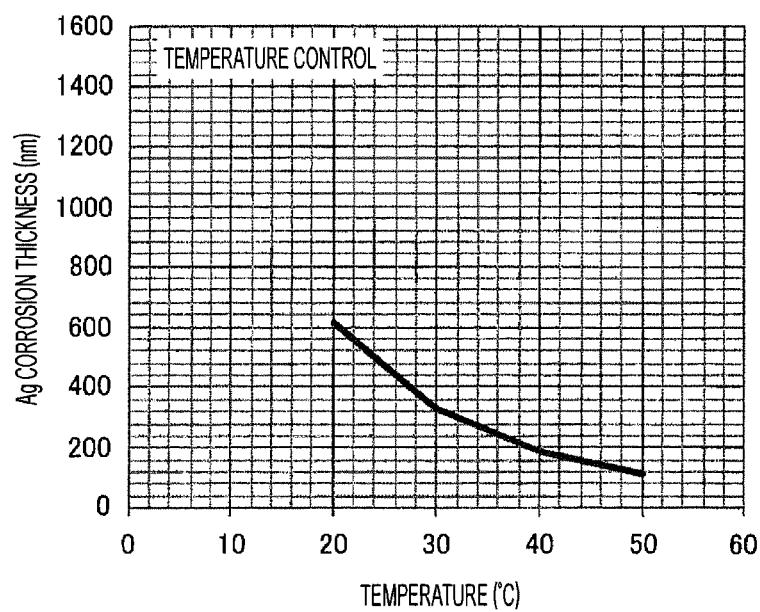
FIG. 16 is a graph illustrating a possibility of corrosion prevention only by temperature control.

FIG. 16 is a graph illustrating a possibility of corrosion prevention only by temperature control. A horizontal axis illustrates the inside temperature, and a vertical axis illustrates the corrosion thickness of $H_2S$—$NO_2$-based silver.

It is understood from FIG. 16 that the corrosion can be suppressed by increasing the inside temperature. It is because the inside relative humidity decreases with the increase in the inside temperature.

Figure 17:
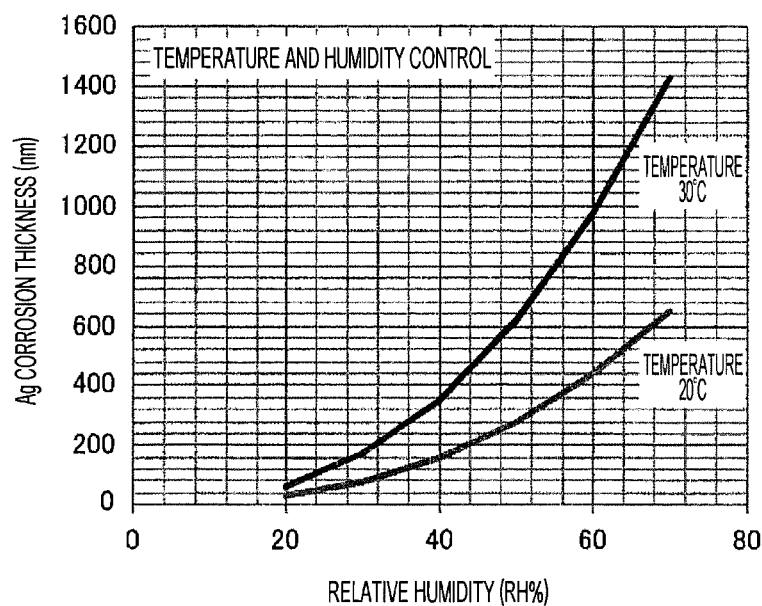
FIG. 17 is a graph illustrating a possibility of corrosion prevention when temperature and humidity are controlled.

FIG. 17 is a graph illustrating a possibility of corrosion prevention when the temperature and the humidity are controlled. A horizontal axis illustrates the inside relative humidity, and a vertical axis illustrates the corrosion thickness of $H_2S$—$NO_2$-based silver.

It is understood from FIG. 17 that corrosion can be suppressed by reducing the inside relative humidity. It is also understood that it is desirable to decrease the inside temperature and decrease the inside relative humidity. Since the absolute humidity in the indoor space is typically equal to the absolute humidity of the outside air, the inside relative humidity depends on the absolute humidity of the outside air, but it is understood from FIG. 17 that it is possible to effectively suppress corrosion not only when the inside temperature is decreased using the air conditioner but also when the absolute humidity in the indoor space is decreased through dehumidification.

As a specific example of preventing corrosion of the electronic device in view of the corrosion thickness of $H_2S$—$NO_2$-based silver, there is an environment condition in which a temperature range is 18° C. to 28° C., an upper limit value of the relative humidity is 60%, and the absolute humidity is 7 $g/m^3$ to 13 $g/m^3$.

Figure 18:
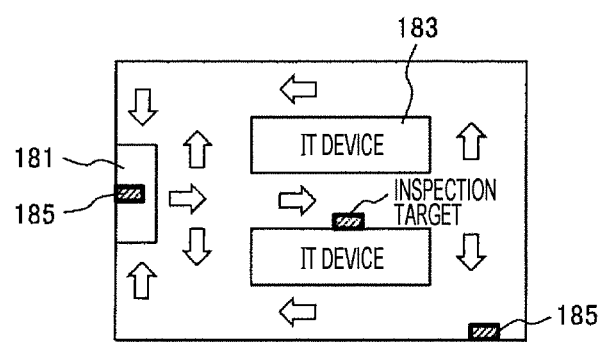
FIG. 18 is a plane view illustrating an arrangement of an electronic part serving as a diagnosis target and a corrosive gas sensor when an occurrence position of corrosive gas is known.

FIG. 18 is a plane view illustrating an arrangement of electronic parts serving as a diagnosis target and corrosion sensors when an occurrence position of corrosive gas is known.

In FIG. 18, an air conditioner 181, an IT device 183 (electronic device) serving as an inspection target, and a corrosion sensor 185 are installed in an indoor space. Since the air conditioner 181 has a ventilatory function and has an air supply opening, the air supply port is a known occurrence position of corrosive gas. Further, since the corrosion sensor 185 is located at a position away from the IT device 183, accurate corrosive gas density around the IT device 183 is unknown. In this regard, the corrosive gas density in the vicinity of the IT device 183 is calculated through a corrosion environment diagnosis process to be described below.

Figure 19:
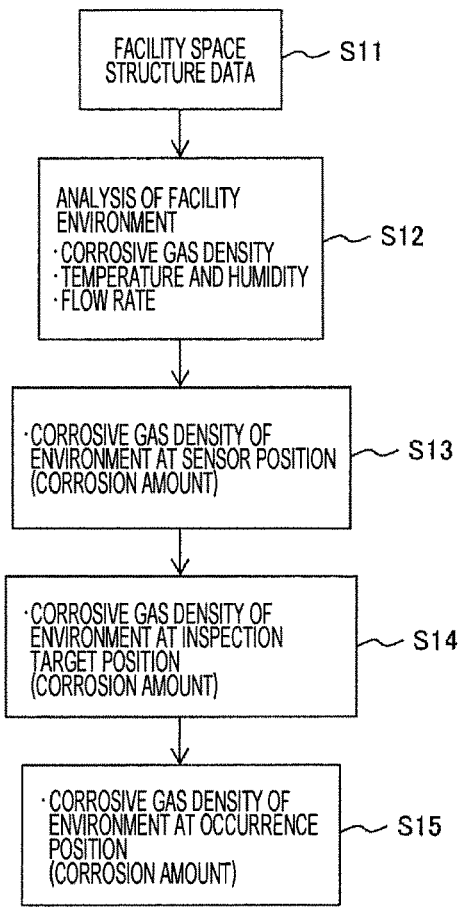
FIG. 19 is a flowchart illustrating a corrosion environment diagnosis process when an occurrence position of corrosive gas is known.

In FIG. 19, the corrosion sensor 185 is installed in the indoor space, but in addition to or instead of the corrosion sensor 185, a gas sensor that measures the corrosive gas density may be installed.

FIG. 19 is a flowchart illustrating the corrosion environment diagnosis process when the occurrence position of corrosive gas is known.

Referring to FIG. 19, facility space, structure data, and the like are input (S11), and the corrosive gas density, the temperature and the humidity, the flow rate, and the like are calculated through analysis of a facility environment (S12). Then, the corrosive gas density (corrosion amount) of the environment at a sensor position is calculated (S13). The corrosive gas density (corrosion amount) of the environment at an inspection target position is calculated on the basis of the corrosive gas density (corrosion amount) of the environment at the sensor position (S14). Then, the corrosive gas density (corrosion amount) of the environment at an occurrence position is calculated (S15).

Figure 20:
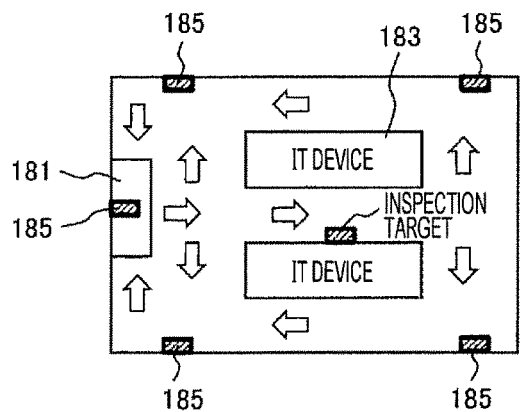
FIG. 20 is a plane view illustrating an arrangement of an electronic part serving as a diagnosis target and a corrosive gas sensor when an occurrence position of corrosive gas is unknown.

FIG. 20 is a plane view illustrating an arrangement of electronic parts serving as a diagnosis target and corrosion sensors when the occurrence position of corrosive gas is unknown.

In FIG. 20, an air conditioner 181, an IT device 183 (electronic device) serving as an inspection target, and a plurality of corrosion sensors 185 are installed in an indoor space. The occurrence position of corrosive gas is not specified. Further, since the corrosion sensor 185 is located at a position away from the IT device 183, the exact corrosive gas density in the vicinity of the IT device 183 is unknown. In this regard, the corrosive gas density in the vicinity of the IT device 183 is calculated through a corrosion environment diagnosis process to be described below.

In FIG. 20, the corrosion sensor 185 is installed in an indoor space, but in addition to or instead of the corrosion sensor 185, a gas sensor that measures the corrosive gas density may be installed.

Figure 21:
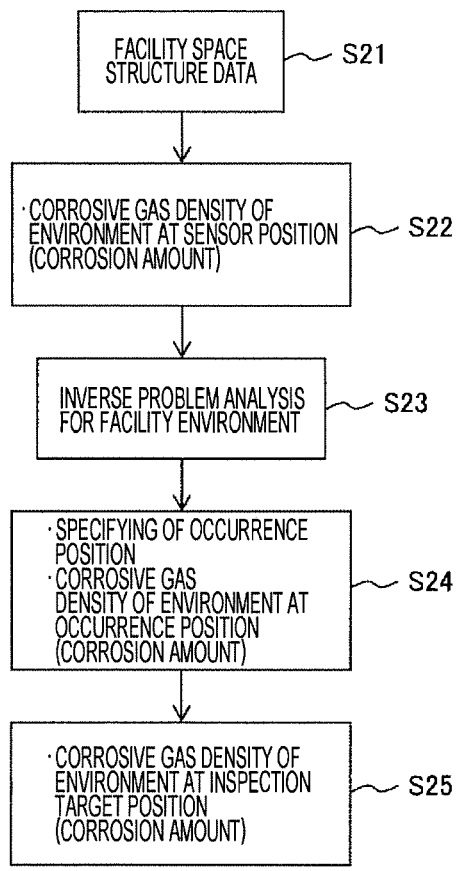
FIG. 21 is a flowchart illustrating a corrosion environment diagnosis process when an occurrence position of corrosive gas is unknown.

FIG. 21 is a flowchart illustrating the corrosion environment diagnosis process when the occurrence position of corrosive gas is unknown.

Referring to FIG. 21, facility space, structure data, and the like are input (S21). Then, the corrosive gas density (corrosion amount) of the environment at the sensor position is calculated (S22). Then, the occurrence position of the corrosive gas is specified by performing an inverse problem analysis for the facility environment is performed (S23), and the corrosive gas density (corrosion amount) of the environment at the occurrence position is calculated (S24). The corrosive gas density (corrosion amount) of the environment at the inspection target position is calculated on the basis of the corrosive gas density (corrosion amount) of the environment at the occurrence position (S25).

Figure 22:
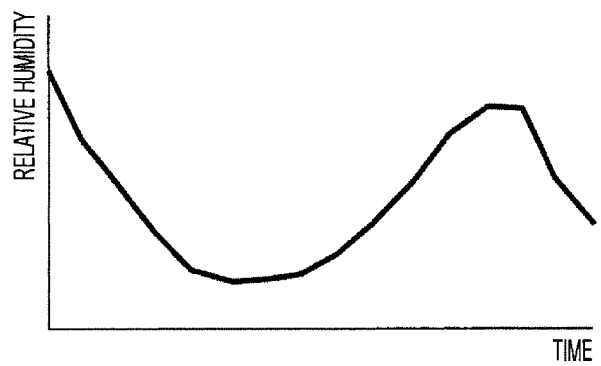
FIG. 22 is a graph illustrating an example of a temporal change in relative humidity.

FIG. 22 is a graph illustrating an example of a temporal change in the relative humidity.

As illustrated in FIG. 22, since the relative humidity in the indoor space corresponds to the absolute humidity of the outside air, there is a day-and-night variation even during one day, and there is a seasonal variation such as summer and winter.

Figure 23:
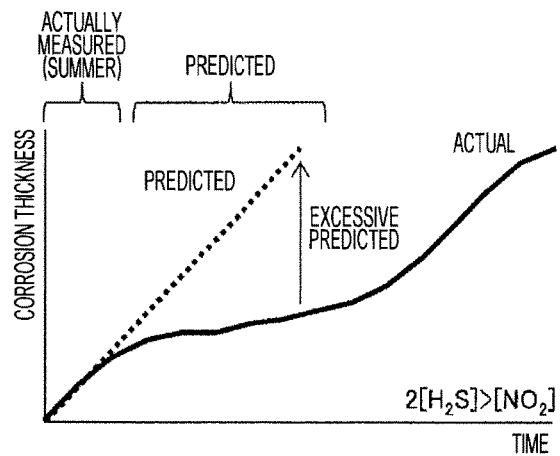
FIG. 23 is a graph illustrating a difference between a predicted corrosion thickness and an actual corrosion thickness in summer under a condition that there is a large amount of hydrogen sulfide.

FIG. 23 is a graph illustrating a difference between a predicted corrosion thickness and an actual corrosion thickness in summer under a condition that there is a large amount of hydrogen sulfide. Since FIG. 23 illustrates a condition that there is a large amount of hydrogen sulfide, the corrosion thickness depends on the relative humidity as illustrated in FIG. 8A.

In summer, because the absolute humidity of the outside air is high, the inside relative humidity increases as well. When there is a large amount of hydrogen sulfide, the corrosion thickness increases as the inside relative humidity increases, and thus when a subsequent corrosion thickness is predicted using only actual measurement data in summer, the corrosion thickness tends to be more excessively predicted than the actual corrosion thickness as illustrated in FIG. 23.

Figure 24:
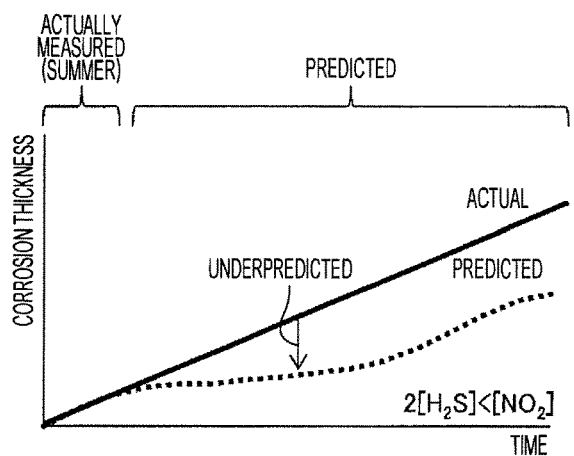
FIG. 24 is a graph illustrating a difference between a predicted corrosion thickness and an actual corrosion thickness in summer under a condition that there is a small amount of hydrogen sulfide.

FIG. 24 is a graph illustrating a difference between a predicted corrosion thickness and an actual corrosion thickness in summer under a condition that there is a small amount of hydrogen sulfide. Since FIG. 24 illustrates a condition that there is a small amount of hydrogen sulfide, the corrosion thickness does not depend on the relative humidity as illustrated in FIG. 8B.

When there is a small amount of hydrogen sulfide, the corrosion thickness does not depend on the inside relative humidity. Therefore, when a subsequent corrosion thickness is predicted using only actual measurement data in summer under the assumption that there is humidity dependency, the corrosion rate in winter is estimated to be low. For this reason, the corrosion thickness tends to be predicted to be much smaller than the actual corrosion thickness as illustrated in FIG. 24.

Figure 25:
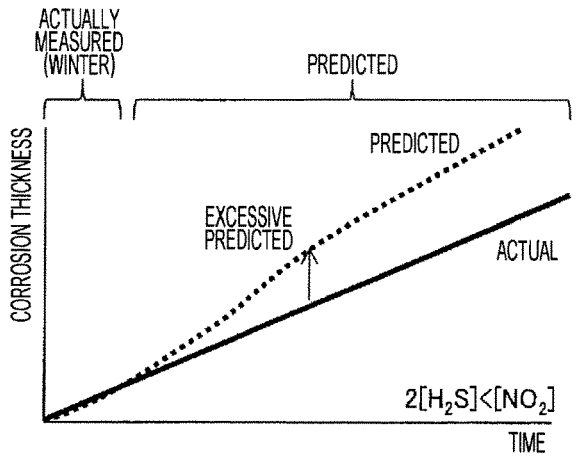
FIG. 25 is a graph illustrating a difference between a predicted corrosion thickness and an actual corrosion thickness in winter under a condition that there is a small amount of hydrogen sulfide.

FIG. 25 is a graph illustrating a difference between a predicted corrosion thickness and an actual corrosion thickness in winter under a condition that there is a small amount of hydrogen sulfide. Since FIG. 25 illustrates a condition that there is a small amount of hydrogen sulfide, the corrosion thickness does not depend on the relative humidity as illustrated in FIG. 8B.

When a subsequent corrosion thickness is predicted using only actual measurement data in winter under the assumption that there is humidity dependency, the corrosion rate in summer is estimated to be high. For this reason, the corrosion thickness tends to be predicted to be much larger than the actual corrosion thickness as illustrated in FIG. 25.

The effects of the present invention will be described below.

According to the present invention, it is possible to estimate future indoor environment data in accordance with actual circumstances, and thus it is possible to estimate a future corrosion amount of the diagnosis target with a high degree of accuracy. In other words, it is possible to obtain, for example, a temperature difference and a humidity difference between outside air environment data and indoor environment data and a periodic change thereof from a correspondence relation between outside air environment data and indoor environment data in the same period as a set period, apply the temperature difference, the humidity difference, and the periodic change to previous outside air environment data, and estimate future indoor environment data in which the periodic change of the indoor environment data and influence of the outside air environment data are considered.

Since the corrosion amount has the temperature and the humidity as a factor, if it is possible to estimate the future indoor environment data accurately in accordance with actual circumstances, it is possible to estimate the future corrosion amount accurately. Particularly, according to the present invention, it is found out that the corrosion mechanism differs depending on the ratio of the hydrogen sulfide density and the nitrogen dioxide density in the environment, and it is possible to obtain a correlation between the indoor environment data and the corrosion thickness data recorded in the set period on the basis of the corrosion mechanism and estimate the future corrosion amount accurately.

Further, the set period is commonly one to three months, but it is desirable that the set period be three or more months for the sake of high accuracy estimation. In the case of simple estimation, the set period may be about one week, but in this case, it is desirable to use an electric resistive type sensor or a QCM sensor which is a highly accurate corrosion sensor. Further, for example, meteorological statistical information published by a meteorological agency may be used as the outside air environment database.

When the installation environment of the electronic device is subject to air conditioning control, the temperature and the humidity in the indoor space are the temperature and the humidity which are set by the air conditioning device. In this case, preferably, a corrosion environment diagnosis system is configured to include a temperature sensor that measures temperature in an air conditioning room in which an electronic device including an electronic part serving as a diagnosis target is installed, a humidity sensor that measures humidity in the room, a corrosion sensor that measures a corrosion amount of the diagnosis target, a diagnostic processing device that records indoor environment data including the temperature and the humidity in the room measured by the sensors and corrosion data of the diagnosis target during a set period, estimates a future corrosion amount of the diagnosis target on the basis of the recorded indoor environment data and the corrosion data, and performs deterioration diagnosis, and an air conditioning database in which air conditioning data including temperature and humidity set in an air conditioning device is recorded, wherein the diagnostic processing device obtains a correlation relation between the indoor environment data and the corrosion data recorded during the set period, estimates the future indoor environment data on the basis of a correspondence relation between the indoor environment data and the air conditioning data, and estimates the future corrosion amount of the diagnosis target from the estimated indoor environment data and the correlation.

Accordingly, similarly to the case of the outside air environment data, it is possible to accurately estimate changes in temperature and humidity in an indoor space in the future in accordance with the temperature and the humidity set in the air conditioning device, and it is possible to accurately estimate the corrosion amount as well. Further, when the installation environment of the electronic device is subject to the air conditioning control, it is desirable to use the air conditioning database, similarly to the estimation of the corrosion amount.

According to the present invention, it is possible to accurately estimate the future corrosion amount, and it is possible to promptly develop an anti-corrosion countermeasure in accordance with a degree of corrosiveness.

REFERENCE SIGNS LIST 1 corrosion environment diagnosis system
2 environment measuring device
3 electronic device
4 diagnostic processing device
6 outside air environment database
8 diagnosis result output device
12 temperature sensor
14 humidity sensor
16 gas sensor
18 corrosion sensor
22 database
30 environment classifying unit
32 environment estimating unit
34 damage estimating unit
36 environment diagnosing unit
40 corrosion database
101 corrosive gas database
103 air conditioner setting value
181 air conditioner
183 IT device
185 corrosion sensor

The invention claimed is:

1. A corrosion environment diagnosis system, comprising:
an environment measuring device that includes a temperature sensor that measures temperature in an electronic part serving as a diagnosis target or an indoor space in which an electronic device including the electronic part is installed,
a humidity sensor that measures relative humidity in the indoor space or the electronic device,
a corrosion sensor that measures a corrosion thickness of the diagnosis target, and a database in which indoor environment data including the temperature and the relative humidity measured by the temperature sensor and the humidity sensor and corrosion thickness data including the corrosion thickness measured by the corrosion sensor are accumulated;
an outside air environment database in which outside air environment data including previous temperature and humidity of outside air is recorded; and
a diagnostic processing device comprising a processor configured to receive data of the outside air environment database and the environment measuring device,
wherein the processor of the diagnostic processing device determines a corrosion mechanism indicating a relation between the corrosion thickness and the relative humidity on the basis of the indoor environment data, the corrosion thickness data, and the outside air environment data, and estimates a future corrosion thickness of the diagnosis target,
wherein corrosive gas involved in the corrosion mechanism includes a hydrogen sulfide and a nitrogen dioxide, and
wherein the corrosion mechanism includes a first mechanism that depends on the temperature and the relative humidity in the indoor space and a second mechanism that does not depend on the temperature and the relative humidity in the indoor space.

2. The corrosion environment diagnosis system according to claim 1,
wherein the processor of the diagnostic processing device calculates a corrosion rate and estimates the future corrosion thickness.

3. A corrosion environment diagnosis system, comprising:
an environment measuring device that includes a temperature sensor that measures temperature in an electronic part serving as a diagnosis target or an indoor space in which an electronic device including the electronic part is installed, a humidity sensor that measures relative humidity in the indoor space or the electronic device, a corrosion sensor that measures a corrosion thickness of the diagnosis target, a gas sensor that measures density of corrosive gas in the indoor space, and a database in which indoor environment data including the temperature and the relative humidity measured by the temperature sensor and the humidity sensor, corrosion thickness data including the corrosion thickness measured by the corrosion sensor, and the density of the corrosive gas measured by the gas sensor are accumulated;
an outside air environment database in which outside air environment data including previous temperature and humidity of outside air is recorded; and
a diagnostic processing device comprising a processor configured to receive data of the outside air environment database and the environment measuring device,
wherein the corrosive gas includes a hydrogen sulfide and a nitrogen dioxide,
wherein the processor of the diagnostic processing device calculates a ratio of density of the hydrogen sulfide and density of the nitrogen dioxide measured by the gas sensor, decides a corrosion mechanism from the ratio, and estimates a future corrosion thickness of the diagnosis target,
wherein the processor of the diagnostic processing device calculates a corrosion rate and estimates the future corrosion thickness, and
wherein the processor of the diagnostic processing device determines that the corrosion rate depends on the temperature and the relative humidity in the indoor space when the ratio is higher than ½, and determines that the corrosion rate does not depend on the temperature and the relative humidity in the indoor space when the ratio is ½ or less.

4. The corrosion environment diagnosis system according to claim 3,
wherein, when the ratio is higher than ½, the processor of the diagnostic processing device assumes that the corrosion mechanism is a mechanism in which a chemical reaction of producing sulfur from the hydrogen sulfide and a part of the nitrogen dioxide and an electrochemical reaction in which the hydrogen sulfide and oxygen in the air are involved progress in parallel, and when the ratio is ½ or less, the processor of the diagnostic processing device assumes that the corrosion mechanism is a mechanism in which a chemical reaction of producing sulfur from the hydrogen sulfide and a part of the nitrogen dioxide is a main reaction.

5. The corrosion environment diagnosis system according to claim 4,
wherein the corrosion sensor is an electrical resistive type sensor or quartz crystal microbalance sensor.

6. A corrosion environment diagnosis system, comprising:
an environment measuring device that includes a temperature sensor that measures temperature in an electronic part serving as a diagnosis target or an indoor space in which an electronic device including the electronic part is installed, a humidity sensor that measures relative humidity in the indoor space or the electronic device, a corrosion sensor that measures a corrosion thickness of the diagnosis target, and a database in which indoor environment data including the temperature and the relative humidity measured by the temperature sensor and the humidity sensor and corrosion thickness data including the corrosion thickness measured by the corrosion sensor are accumulated;

an air conditioner that adjusts the temperature and the humidity in the indoor space;

an air conditioning database in which air conditioning data including set temperature and set humidity of the air conditioner is recorded; and a diagnostic processing device comprising a processor and configured to receive data of the air conditioning database and the environment measuring device, wherein the processor of the diagnostic processing device determines a corrosion mechanism indicating a relation between the corrosion thickness and the relative humidity on the basis of the indoor environment data, the corrosion thickness data, and the air conditioning data, and estimates a future corrosion thickness of the diagnosis target, wherein corrosive gas involved in the corrosion mechanism includes a hydrogen sulfide and a nitrogen dioxide, and wherein the corrosion mechanism includes a first mechanism that depends on the temperature and the relative humidity in the indoor space and a second mechanism that does not depend on the temperature and the relative humidity in the indoor space.

7. The corrosion environment diagnosis system according to claim 6, wherein the processor of the diagnostic processing device calculates a corrosion rate and estimates the future corrosion thickness.

8. A corrosion prevention system that prevents corrosion of the electronic part by using the corrosion environment diagnosis system according to claim 7, wherein the air conditioner adjusts the relative humidity so that the future corrosion thickness is decreased.

9. The corrosion prevention system according to claim 8, wherein the air conditioner maintains the relative humidity to be 60% or less.

10. A corrosion environment diagnosis method, comprising:

accumulating indoor environment data and corrosion thickness data, the indoor environment data including temperature measured by a temperature sensor and relative humidity measured by a humidity sensor, the temperature sensor measuring the temperature in an electronic part serving as a diagnosis target or an indoor space in which an electronic device including the electronic part is installed, the humidity sensor measuring the relative humidity in the indoor space or the electronic device, the corrosion thickness data including a corrosion thickness of the diagnosis target measured by a corrosion sensor that measures the corrosion thickness; and determining a corrosion mechanism indicating a relation between the corrosion thickness and the relative humidity on the basis of the indoor environment data, the corrosion thickness data, and outside air environment data in which outside air environment data including previous temperature and humidity of outside air is recorded and estimating a future corrosion thickness of the diagnosis target, wherein corrosive gas involved in the corrosion mechanism includes a hydrogen sulfide and a nitrogen dioxide, and wherein the corrosion mechanism includes a first mechanism that depends on the temperature and the relative humidity in the indoor space and a second mechanism that does not depend on the temperature and the relative humidity in the indoor space.

11. A corrosion prevention method, comprising:

accumulating indoor environment data and corrosion thickness data, the indoor environment data including temperature measured by a temperature sensor and relative humidity measured by a humidity sensor, the temperature sensor measuring the temperature in an electronic part serving as a diagnosis target or an indoor space in which an electronic device including the electronic part is installed, the humidity sensor measuring the relative humidity in the indoor space or the electronic device, the corrosion thickness data including a corrosion thickness of the diagnosis target measured by a corrosion sensor that measures the corrosion thickness;

determining a corrosion mechanism indicating a relation between the corrosion thickness and the relative humidity on the basis of the indoor environment data, the corrosion thickness data, and outside air environment data in which outside air environment data including previous temperature and humidity of outside air is recorded and estimating a future corrosion thickness of the diagnosis target; and adjusting the relative humidity so that the future corrosion thickness is decreased, wherein corrosive gas involved in the corrosion mechanism includes a hydrogen sulfide and a nitrogen dioxide, and wherein the corrosion mechanism includes a first mechanism that depends on the temperature and the relative humidity in the indoor space and a second mechanism that does not depend on the temperature and the relative humidity in the indoor space.

* * * * *